(12) United States Patent
Hartwell

(10) Patent No.: US 12,082,999 B2
(45) Date of Patent: *Sep. 10, 2024

(54) WOUND CLOSURE DEVICE AND METHOD OF USE

(71) Applicant: Smith & Nephew PLC, Watford (GB)

(72) Inventor: Edward Yerbury Hartwell, Hull (GB)

(73) Assignee: Smith & Nephew PLC, Watford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/397,981

(22) Filed: Dec. 27, 2023

(65) Prior Publication Data

US 2024/0122765 A1    Apr. 18, 2024

Related U.S. Application Data

(63) Continuation of application No. 16/622,248, filed as application No. PCT/EP2018/065397 on Jun. 11, 2018, now Pat. No. 11,872,110.

(60) Provisional application No. 62/518,752, filed on Jun. 13, 2017.

(51) Int. Cl.
| | |
|---|---|
| *A61F 13/05* | (2024.01) |
| *A61B 17/08* | (2006.01) |
| *A61F 13/00* | (2024.01) |
| *A61F 13/02* | (2024.01) |

(Continued)

(52) U.S. Cl.
CPC .............. *A61F 13/05* (2024.01); *A61B 17/08* (2013.01); *A61F 13/022* (2013.01); *A61F 13/0266* (2013.01); *A61F 13/0273* (2013.01); *A61M 1/913* (2021.05); *A61B 2017/081* (2013.01); *A61F 2013/00174* (2013.01); *A61F 2013/00536* (2013.01); *A61M 1/90* (2021.05)

(58) Field of Classification Search
CPC ............ A61F 13/0216; A61F 13/00068; A61F 13/0266; A61F 2013/00174; A61F 2013/00536; A61M 1/90; A61B 17/08; A61B 2017/081
See application file for complete search history.

(56) References Cited

U.S. PATENT DOCUMENTS

| | | |
|---|---|---|
| 3,194,239 A | 7/1965 | Sullivan et al. |
| 3,789,851 A | 2/1974 | LeVeen |
| 4,467,805 A | 8/1984 | Fukuda |

(Continued)

FOREIGN PATENT DOCUMENTS

| | | |
|---|---|---|
| AU | 2012261793 B2 | 11/2014 |
| AU | 2013206230 B2 | 5/2016 |

(Continued)

OTHER PUBLICATIONS

"Definition of 3D Printer," American Heritage Dictionary of the English Language, Fifth Edition, accessed on Feb. 22, 2018 from URL: https://www.thefreedictionary.com , 2016, 1 page.

(Continued)

*Primary Examiner* — Jessica Arble
(74) *Attorney, Agent, or Firm* — Knobbe, Martens, Olson & Bear, LLP

(57) ABSTRACT

A negative pressure wound closure system and methods for using such a system are described. Preferred embodiments of the invention facilitate closure of the wound by preferentially contracting to exert force on the tissue. Some embodiments may utilize a clamping structure with removable sections.

19 Claims, 36 Drawing Sheets

(51) Int. Cl.
  *A61F 13/0203* (2024.01)
  *A61M 1/00* (2006.01)

(56) References Cited

U.S. PATENT DOCUMENTS

| | | | |
|---|---|---|---|
| 4,608,041 A | 8/1986 | Nielsen |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 6,176,868 B1 | 1/2001 | Detour |
| 6,503,208 B1 | 1/2003 | Skovlund |
| 6,548,727 B1 | 4/2003 | Swenson |
| 6,566,575 B1 | 5/2003 | Stickels et al. |
| 6,685,681 B2 | 2/2004 | Lockwood et al. |
| 6,770,794 B2 | 8/2004 | Fleischmann |
| 6,787,682 B2 | 9/2004 | Gilman |
| 6,977,323 B1 | 12/2005 | Swenson |
| 7,004,915 B2 | 2/2006 | Boynton et al. |
| 7,144,390 B1 | 12/2006 | Hannigan et al. |
| 7,315,183 B2 | 1/2008 | Hinterscher |
| 7,351,250 B2 | 4/2008 | Zamierowski |
| 7,361,184 B2 | 4/2008 | Joshi |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,683,667 B2 | 3/2010 | Kim |
| 7,700,819 B2 | 4/2010 | Ambrosio et al. |
| 7,754,937 B2 | 7/2010 | Boehringer et al. |
| 7,779,625 B2 | 8/2010 | Joshi et al. |
| 7,815,616 B2 | 10/2010 | Boehringer et al. |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,114,126 B2 | 2/2012 | Heaton et al. |
| 8,123,781 B2 | 2/2012 | Zamierowski |
| 8,142,419 B2 | 3/2012 | Heaton et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann |
| 8,430,867 B2 | 4/2013 | Robinson et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,608,776 B2 | 12/2013 | Coward et al. |
| 8,632,523 B2 | 1/2014 | Eriksson et al. |
| 8,663,311 B2 | 3/2014 | Besselink et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,945,030 B2 | 2/2015 | Weston |
| 9,044,579 B2 | 6/2015 | Blott et al. |
| 9,061,095 B2 | 6/2015 | Adie et al. |
| 9,180,231 B2 | 11/2015 | Greener |
| 9,408,755 B2 | 8/2016 | Larsson |
| 9,421,132 B2 | 8/2016 | Dunn |
| 9,655,807 B2 | 5/2017 | Locke et al. |
| 9,849,023 B2 | 12/2017 | Hall et al. |
| 10,143,485 B2 | 12/2018 | Locke et al. |
| 11,324,876 B2 * | 5/2022 | Hartwell .......... A61F 13/05 |
| 11,872,110 B2 * | 1/2024 | Hartwell .......... A61F 13/022 |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0162512 A1 | 8/2004 | Liedtke et al. |
| 2004/0267312 A1 | 12/2004 | Kanner et al. |
| 2005/0142331 A1 | 6/2005 | Anderson et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0069357 A1 | 3/2006 | Marasco |
| 2006/0155260 A1 | 7/2006 | Blott et al. |
| 2006/0217795 A1 | 9/2006 | Besselink et al. |
| 2006/0271018 A1 | 11/2006 | Korf |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |
| 2008/0306456 A1 | 12/2008 | Riesinger |
| 2009/0005716 A1 | 1/2009 | Abuzaina |
| 2009/0099519 A1 | 4/2009 | Kaplan |
| 2009/0105670 A1 | 4/2009 | Bentley et al. |
| 2009/0204423 A1 | 8/2009 | DeGheest et al. |
| 2009/0312685 A1 | 12/2009 | Olsen et al. |
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |

(56) References Cited

U.S. PATENT DOCUMENTS

| | | |
|---|---|---|
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn |
| 2012/0253302 A1 | 10/2012 | Corley |
| 2013/0023842 A1 | 1/2013 | Song |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0180225 A1* | 6/2014 | Dunn ............... A61F 13/05 604/319 |
| 2014/0249495 A1 | 9/2014 | Mumby et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blucher et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth |
| 2017/0281838 A1 | 10/2017 | Dunn |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2567717 A1 | 3/2013 |
| GB | 2389794 A | 12/2003 |
| GB | 2423019 A | 8/2006 |
| GB | 2489947 A | 10/2012 |
| GB | 2496310 A | 5/2013 |
| JP | S6257560 A | 3/1987 |
| JP | 2012105840 A | 6/2012 |
| RU | 62504 U1 | 4/2007 |
| SU | 1818103 A1 | 5/1993 |
| WO | WO-0185248 A1 | 11/2001 |
| WO | WO-0189392 A2 | 11/2001 |
| WO | WO-0205737 A1 | 1/2002 |
| WO | WO-03003948 A1 | 1/2003 |
| WO | WO-03049598 A2 | 6/2003 |
| WO | WO-2005046761 A1 | 5/2005 |
| WO | WO-2005105174 A1 | 11/2005 |
| WO | WO-2006046060 A2 | 5/2006 |
| WO | WO-2008027449 A2 | 3/2008 |
| WO | WO-2008064502 A1 | 6/2008 |
| WO | WO-2008104609 A1 | 9/2008 |
| WO | WO-2009112062 A1 | 9/2009 |
| WO | WO-2010033725 A2 | 3/2010 |
| WO | WO-2010097570 A1 | 9/2010 |
| WO | WO-2011023384 A1 | 3/2011 |
| WO | WO-2012082716 A2 | 6/2012 |
| WO | WO-2012082876 A1 | 6/2012 |
| WO | WO-2012136707 A1 | 10/2012 |
| WO | WO-2012142473 A1 | 10/2012 |
| WO | WO-2013012381 A1 | 1/2013 |
| WO | WO-2013043258 A1 | 3/2013 |
| WO | WO-2013071243 A2 | 5/2013 |
| WO | WO-2013076450 A1 | 5/2013 |
| WO | WO-2013079947 A1 | 6/2013 |
| WO | WO-2013175309 A1 | 11/2013 |
| WO | WO-2013175310 A2 | 11/2013 |
| WO | WO-2014013348 A2 | 1/2014 |
| WO | WO-2014140578 A1 | 9/2014 |
| WO | WO-2014158526 A1 | 10/2014 |
| WO | WO-2014165275 A1 | 10/2014 |
| WO | WO-2014178945 A1 | 11/2014 |
| WO | WO-2014194786 A1 | 12/2014 |
| WO | WO-2015008054 A1 | 1/2015 |
| WO | WO-2015061352 A2 * | 4/2015 ....... A61F 13/00068 |
| WO | WO-2015109359 A1 | 7/2015 |
| WO | WO-2015110409 A1 | 7/2015 |
| WO | WO-2015110410 A1 | 7/2015 |
| WO | WO-2015169637 A1 | 11/2015 |
| WO | WO-2015193257 A1 | 12/2015 |
| WO | WO-2016018448 A1 | 2/2016 |
| WO | WO-2016176513 A1 | 11/2016 |
| WO | WO-2016179245 A1 | 11/2016 |
| WO | WO-2017106576 A1 | 6/2017 |
| WO | WO-2018038665 A1 | 3/2018 |
| WO | WO-2018041805 A1 | 3/2018 |
| WO | WO-2018044944 A1 | 3/2018 |
| WO | WO-2018044949 A1 | 3/2018 |
| WO | WO-2018085457 A1 | 5/2018 |
| WO | WO-2018140386 A2 | 8/2018 |
| WO | WO-2018237206 A2 | 12/2018 |

OTHER PUBLICATIONS

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

International Preliminary Report on Patentability for Application No. PCT/EP2018/065397, mailed on Dec. 26, 2019, 10 pages.

International Search Report and Written Opinion for Application No. PCT/EP2018/065397, mailed on Jul. 25, 2018, 14 pages.

Kapischke M., et al., "Self-Fixating Mesh for the Lichtenstein Procedure—a Prestudy," Langenbeck's Arch Surg, 2010, vol. 395, pp. 317-322.

* cited by examiner

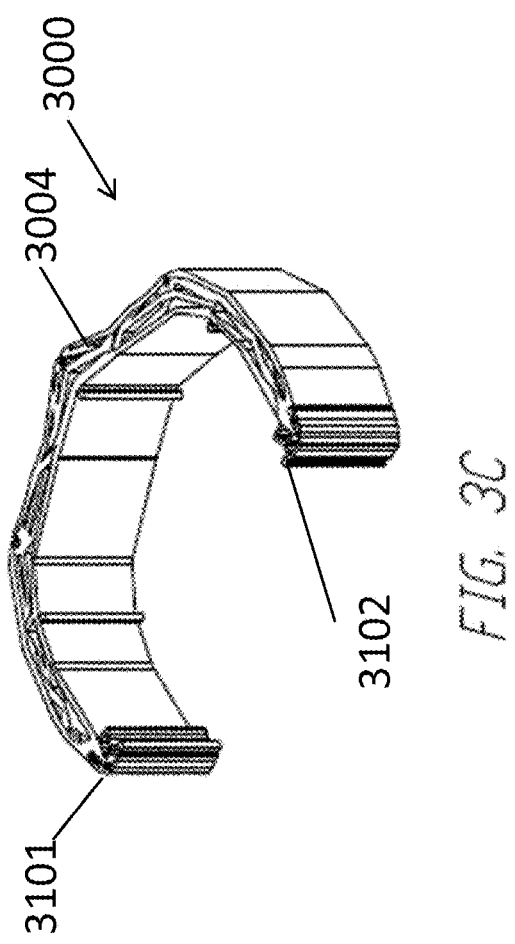

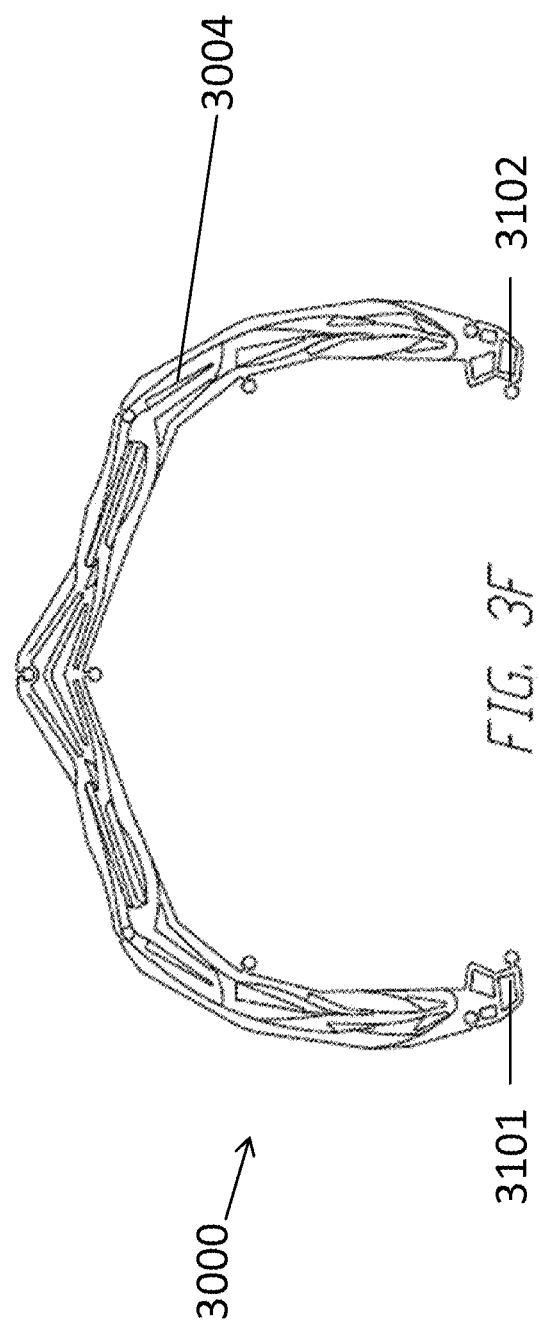

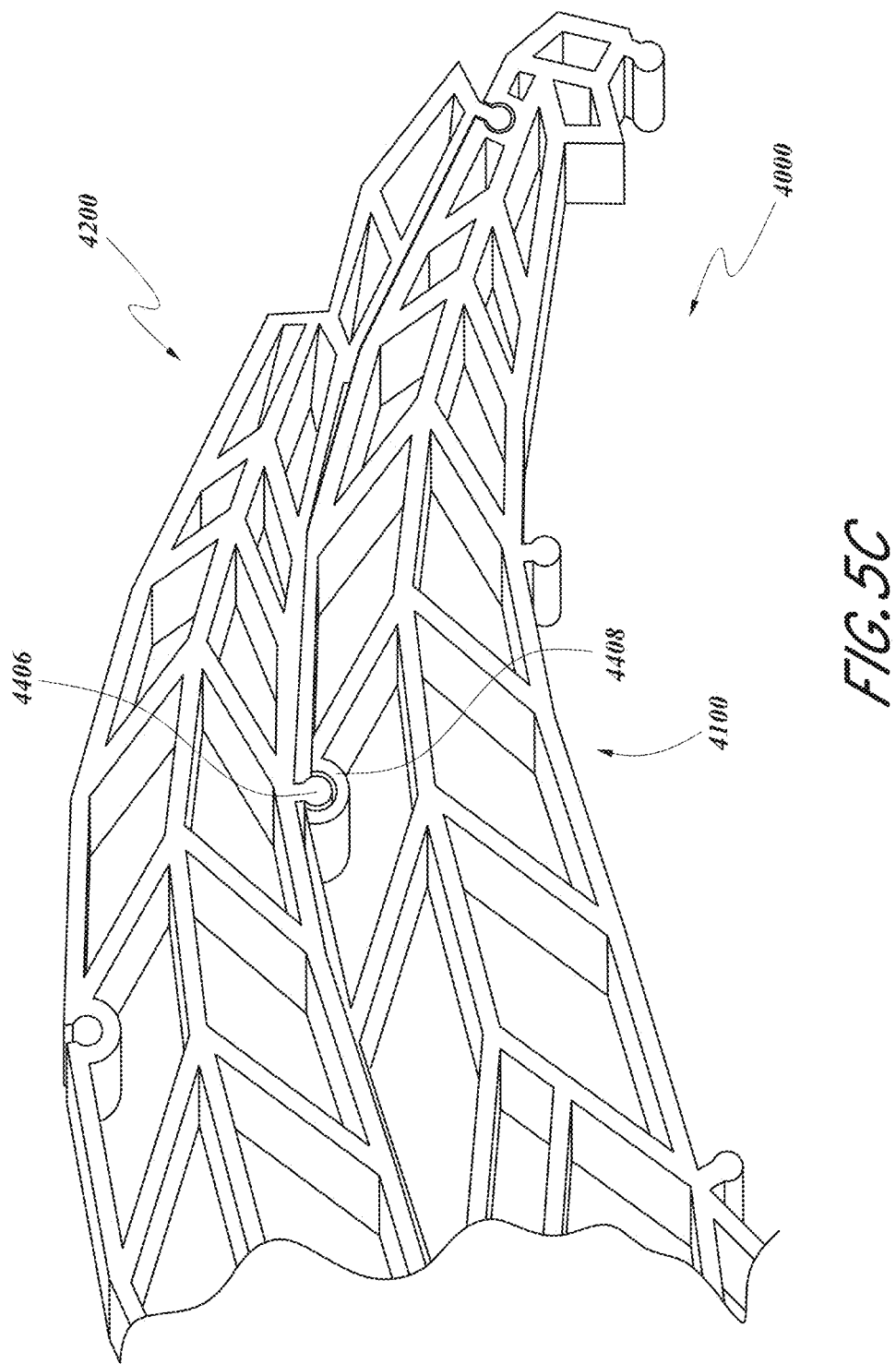

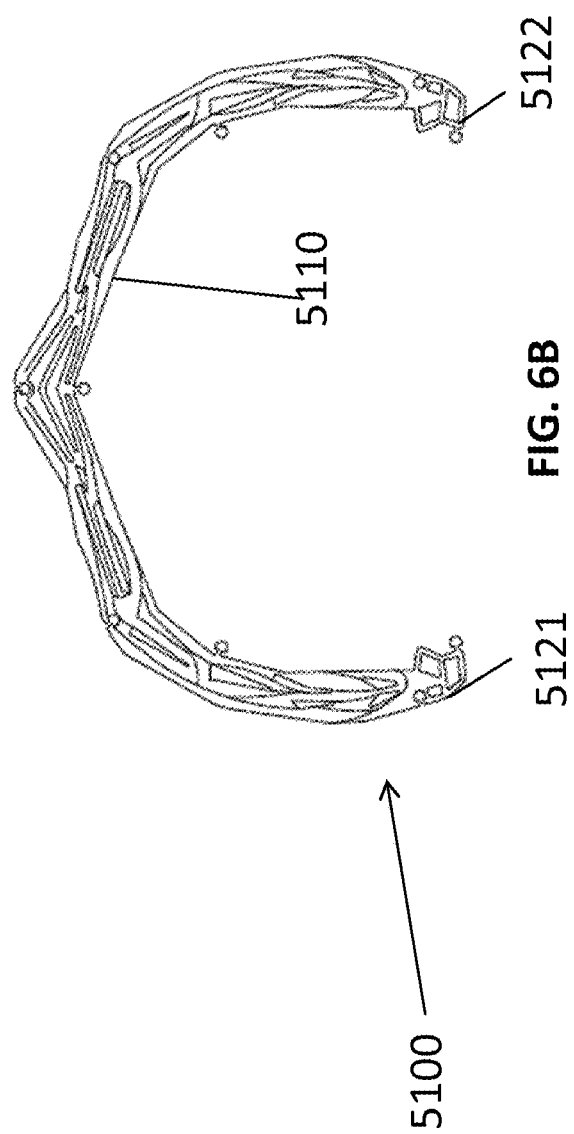

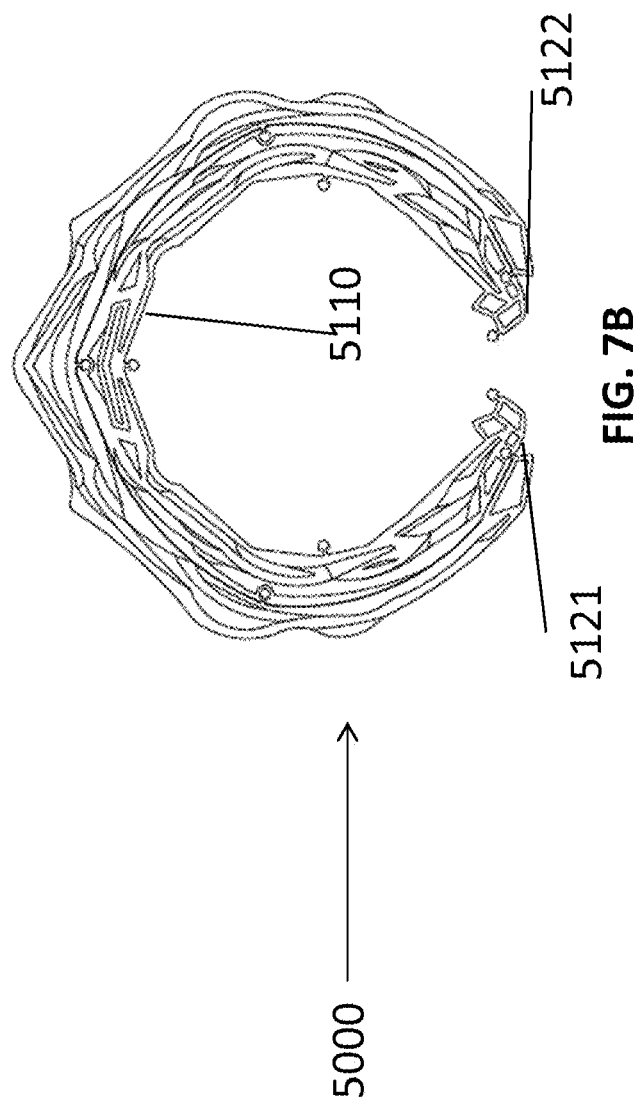

WOUND CLOSURE DEVICE AND METHOD OF USE

CROSS-REFERENCE TO RELATED APPLICATIONS

This application is a continuation of U.S. application Ser. No. 16/622,248, filed Dec. 12, 2019, which is a U.S. national stage application of International Patent Application No. PCT/EP2018/065397, filed Jun. 11, 2018, which claims priority to U.S. Provisional Application No. 62/518,752 filed on Jun. 13, 2017, which is incorporated by reference in its entirety.

BACKGROUND

Field of Use

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases, it can improve the rate of healing while also removing exudates and other deleterious substances from the wound site.

Amputation of lower and upper extremities is one of the oldest known surgically performed procedures. The vast majority of amputations are performed because of artherosclerosis, which is a symptom of diabetes. Less commonly, serious accidents, cardiovascular disease, or the development of a tumor in a limb can lead to the loss of a limb. Amputation procedures require the removal of the diseased tissue in addition to the cutting and shaping of muscle, therefore a large wound is necessarily created on the patient. Closure of such a wound after the underlying edema has subsided, while minimizing the risk of secondary infections and other complications, then becomes a priority.

Other large or incisional wounds at extremities, either as a result of surgery, trauma, or other conditions, may also require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures or staples, there is also a risk that underlying muscular and fascial tissue is not appropriately re-approximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Further, current negative pressure treatment systems may be inadequate for amputation wounds. Typical negative pressure treatment systems are usually directed to wounds on relatively flat body surfaces, while amputation wounds are located at the end of an extremity, often forming a curved surface. Accordingly, there is a need to provide improved apparatuses, methods, and systems for the treatment and closure of amputation wounds.

SUMMARY

Embodiments of the present invention relate to negative pressure wound closure devices, methods, and systems that facilitate closure of a wound. It will be understood by one of skill in the art that the wounds described herein this specification may encompass any wound, and are not limited to a particular location or type of wound. Further, it will be understood by one of skill of art that application of the devices, methods, and systems described herein this specification may be in any manner in relation to negative pressure, and are not limited to the closure of wound or any other particular use. The devices, methods, and systems may operate to reduce the need for repetitive replacement of wound filler material currently employed and can advance the rate of healing. The devices, methods, and systems may be simultaneously used with negative pressure to remove wound fluids.

In certain embodiments, a wound closure device is provided, the device comprises a clamping structure sized and configured to be positioned in or over a wound, the clamping structure having a first end, a second end, a length extending from the first end and the second end, a width transverse to the length extending along a central transverse axis of the clamping structure, and a height transverse to the length and the width. The clamping structure comprises a concave side and a convex side extending the length of the clamping structure from the first end to the second end in parallel or semi-parallel fashion, wherein the concave side is curved or bent concavely with respect to the clamping structure, and the convex side is opposite the concave side and curved or bent convexly with respect to the clamping structure.

A plurality of elongate strips may extend the length of the clamping structure from the first end to the second end, wherein the plurality of elongate strips comprise two outermost elongate strips defining the concave side and the convex side.

A plurality of intervening members may connect the plurality of elongate strips, wherein the plurality of intervening members are configured to pivot relative to the elongate strips to allow the plurality of elongate strips to collapse relative to one another.

A plurality of cells may be provided side-by-side in a horizontal plane parallel to the length and width of the clamping structure, each cell defined by a plurality of walls formed by either the elongate strips or the intervening members, each cell having a top end and a bottom end with an opening extending through the top and bottom ends. The plurality of elongate strips may be configured to increase curvature upon collapse of the plurality of cells and apply a clamping force to the wound.

In certain embodiments, the clamping structure may be at least partially crescent-shaped. The length and width of the clamping structure may be greater than the height of the clamping structure. At least some of the cells may be diamond-shaped.

In certain embodiments, the clamping structure may comprise one or more detachable segments. The one or more detachable segments may comprise attachment elements. The wound closure device may further comprise at least one additional clamping structure.

In certain embodiments, the wound closure device may further comprise a bottom layer of foam configured to conform to concave side of the clamping structure, and/or a top layer of foam configured to conform to the convex side of the clamping structure. The device may further comprise a tissue protection layer.

In certain embodiments, a wound closure device is provided, the device comprising a clamping structure comprising a concave side and a convex side. The clamping structure may be configured to conform to an amputation wound, to apply a closing force to the amputation wound when negative pressure is applied to the clamping structure; and to collapse to a greater extent in a horizontal plane than a vertical plane.

The wound closure device may further comprise a bottom layer of foam attached to the concave side and conforming to the shape of the concave side of the clamping structure; and a top layer of foam attached to the convex side and conforming to the shape of the convex side of the clamping structure.

The clamping structure may be at least partially crescent-shaped. The length and width of the clamping structure may be greater than the height of the structure. The device may further comprise a plurality of cells, wherein at least some of the cells are diamond-shaped. The clamping structure may comprise one or more detachable segments. The one or more detachable segments comprises attachment elements. The device may further comprise at least one additional clamping structure.

In certain embodiments, the wound closure device may further comprise one or more drapes configured to cover the clamping structure and form a seal around the wound. The device may further comprise a suction port configured to supply negative pressure to the wound.

In certain embodiments, the wound closure device may further comprise a negative pressure source configured to supply negative pressure to clamping structure to cause collapse of the plurality of cells and cause the clamping structure to apply the clamping force to the wound.

In certain embodiments, a method of treating a wound is provided, the method comprising: providing a clamping structure of any one of the preceding claims; and placing the clamping structure in or over a wound site wherein the clamping structure is placed so that the concave side of the clamping structure faces the wound and the length of the clamping structure is aligned across the wound opening. The method may further comprise covering the clamping structure with at least one drape sealed to skin surrounding the wound; and applying negative pressure through the at least one drape to the wound via a source of negative pressure, wherein the application of negative pressure causes the clamping structure to collapse. The method may further comprise inserting a tissue protection layer over the wound before placing the clamping structure.

In certain embodiments, a method of closing a wound after limb amputation is provided, the method comprising; providing a clamping structure; inserting a tissue protection layer over the wound; placing the bottom layer of foam over the wound; placing a clamping structure to the wound site wherein the length of the clamping structure is aligned perpendicular to the wound opening; covering the clamping structure with at least one drape sealed to skin surrounding the wound; and applying negative pressure through the at least one drape to the wound via a source of negative pressure, wherein the application of negative pressure causes the clamping structure to collapse.

Other embodiments of an apparatus for use with negative pressure, devices and associated apparatuses are described below.

BRIEF DESCRIPTION OF THE DRAWINGS

FIGS. 3A-C illustrate perspective views of an embodiment of a clamping structure in a natural state, a half-collapsed state, and a collapsed state.

FIGS. 3D-F illustrate top views of an embodiment of a clamping structure in a natural state, a half-collapsed state, and a collapsed state.

FIGS. 5A-I illustrate embodiments of a clamping structure having a detachable segment.

FIGS. 6A-B illustrate an embodiment of an inner segment of a clamping structure in a natural state and a collapsed state.

FIGS. 7A-D illustrate embodiments of a clamping structure having a detachable segment in a natural state and a collapsed state.

DETAILED DESCRIPTION

Figure 1:
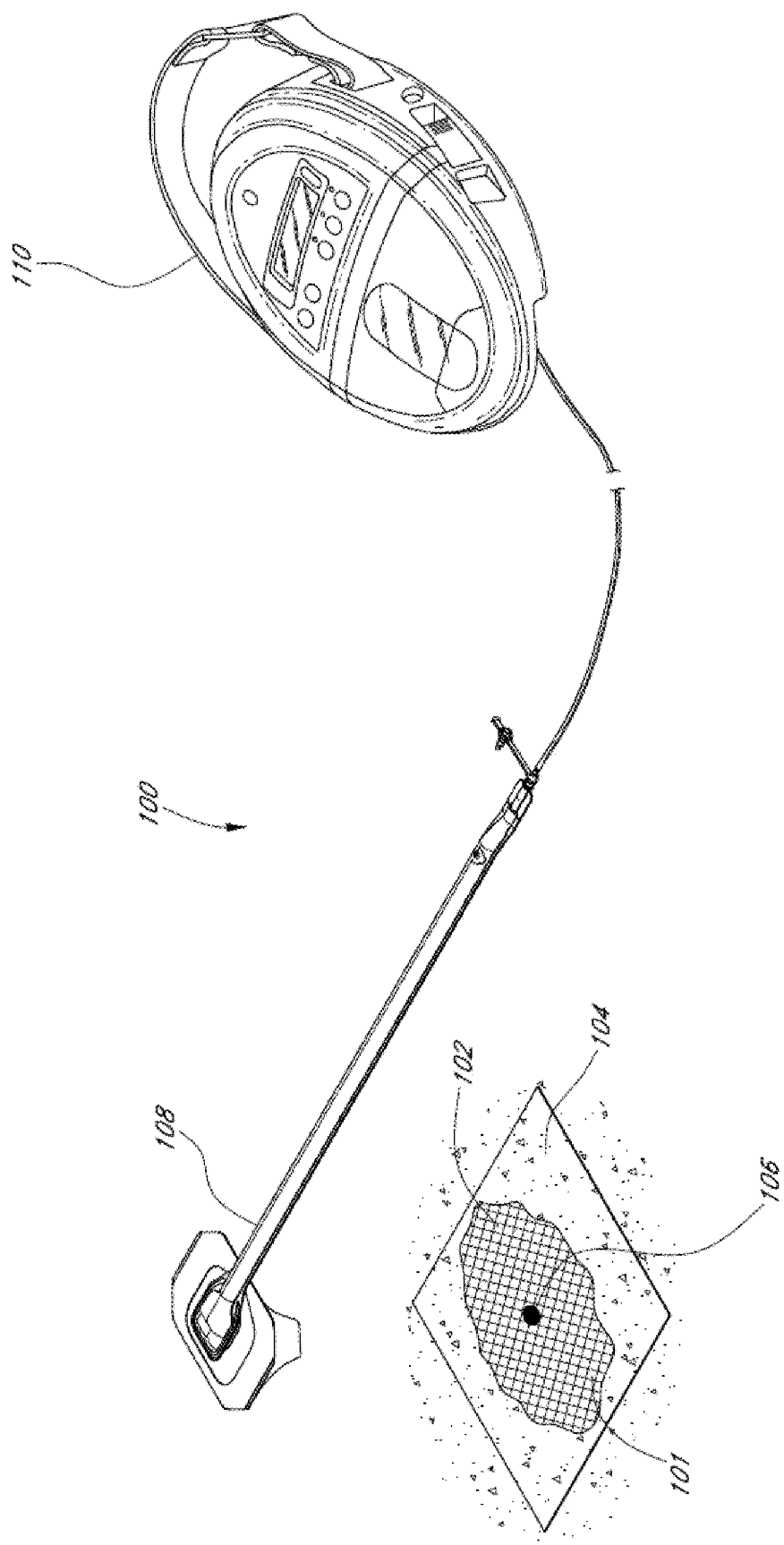
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, amputation wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; PCT App. No. PCT/GB2014/050746, "Compressible Wound Fillers and Systems and Methods of Use In Treating Wounds With Negative Pressure," filed Mar. 13, 2014, published as WO 2014/140578 A1; PCT App. No. PCT/US2014/061627, titled "Negative Pressure Wound Closure Device," filed Oct. 21, 2014, and published as 2016/0287765 A1; and PCT App. No. PCT/US2016/029888, titled "Negative Pressure Wound Closure Device," filed Apr. 28, 2016, published as WO 2016/176513. The entireties of the aforementioned applications are each hereby incorporated by reference and should be considered part of the present specification.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 time, 10 times, 12 times or greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted onto a wound 101. The wound packer 102 may comprise porous materials such as foam, and in some embodiments, may comprise one or more embodiments of wound closure devices or clamping structures described in further detail in this section or elsewhere in this specification. In some embodiments, the perimeter or top of any wound closure device applied on the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In use, the wound 101 may be prepared and cleaned. In some cases, a non- or minimally-adherent tissue protection layer (not illustrated) may be applied over any exposed internal tissue. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Any structure or component disclosed herein this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Figure 2A:
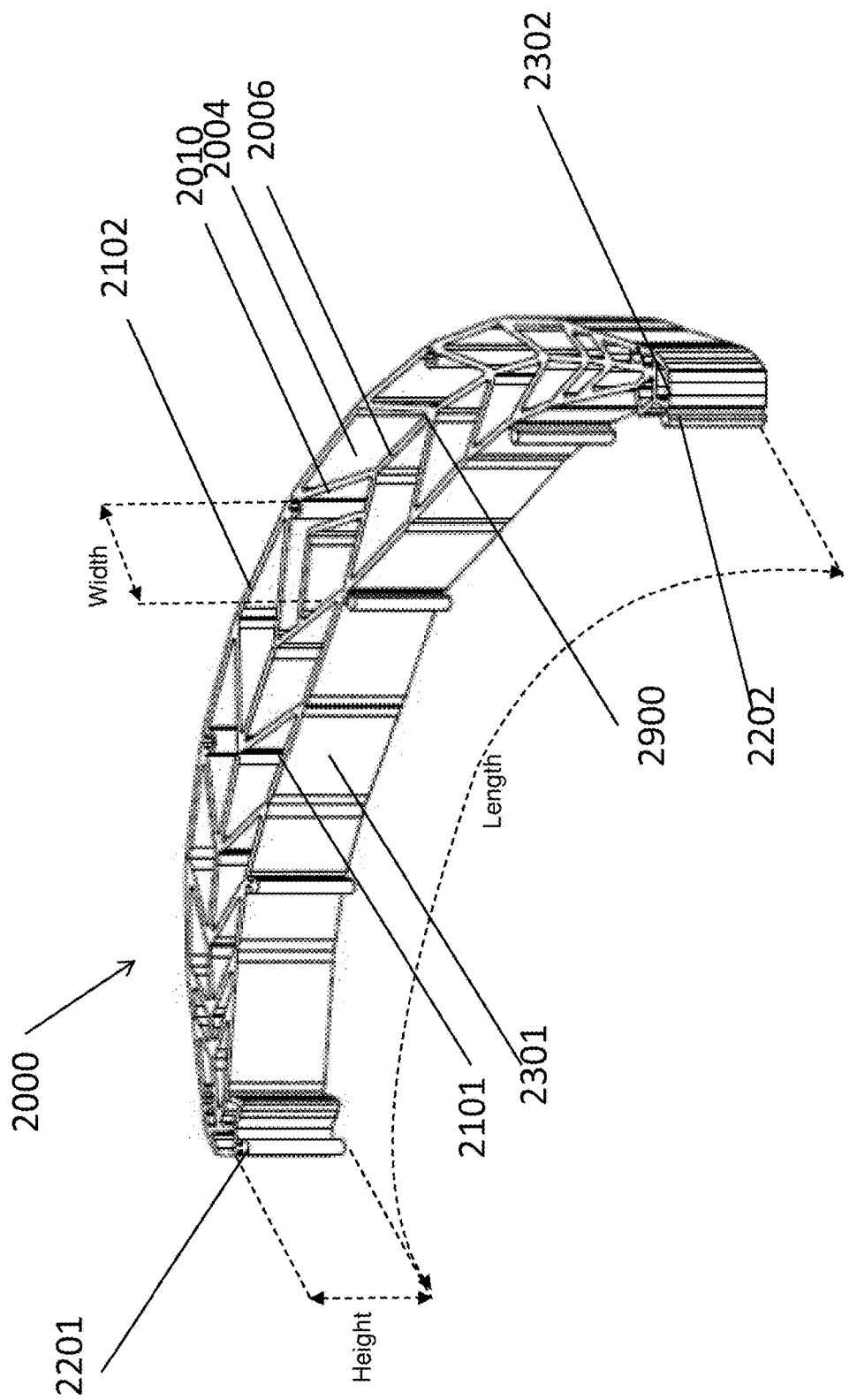
FIG. 2A illustrates a perspective view of an embodiment of a clamping structure.
Figure 2B:
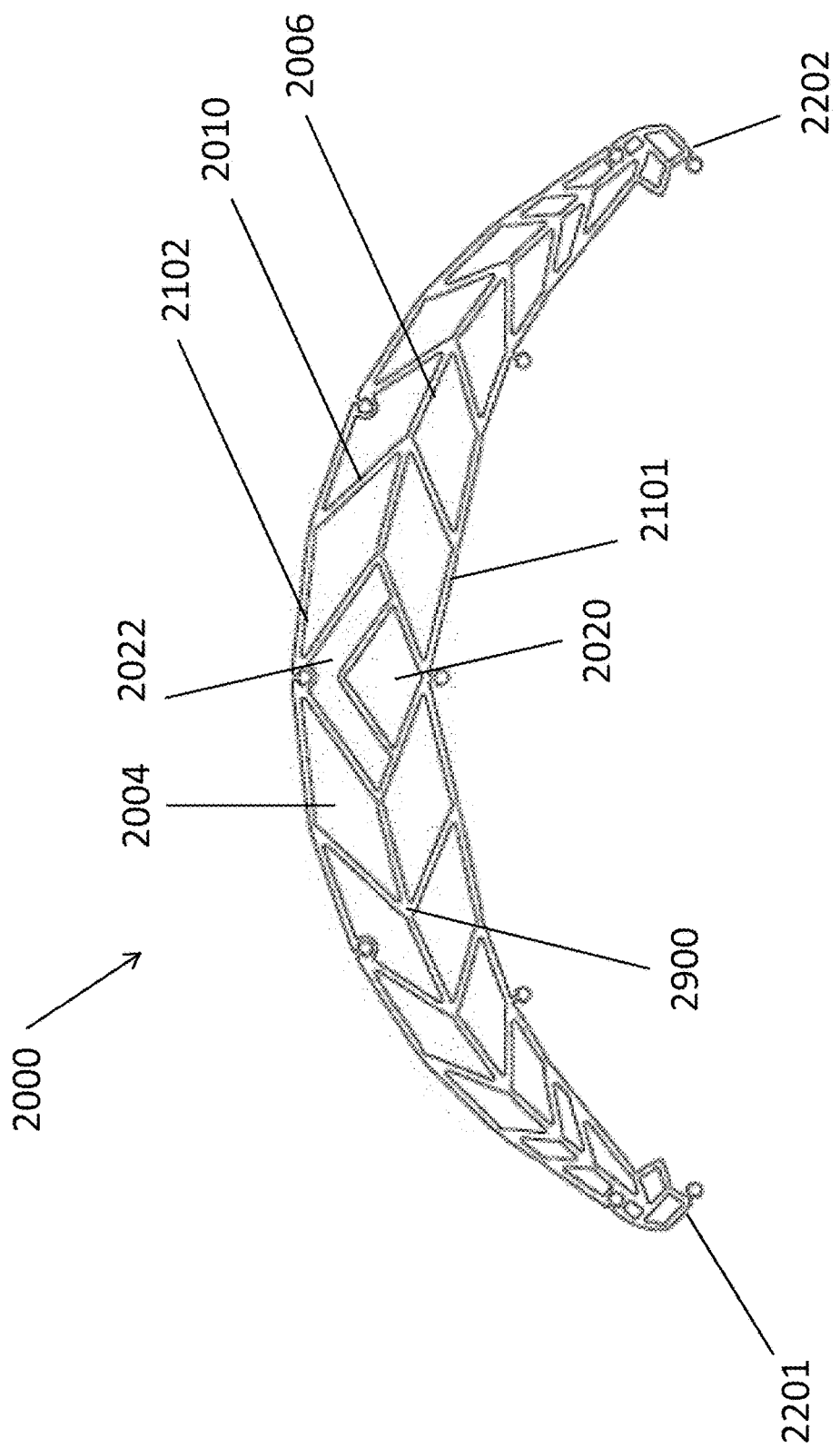
FIG. 2B illustrates a top view of an embodiment of a clamping structure
Figure 2C:
FIG. 2C is a photograph of an embodiment of a clamping structure.

FIGS. 2A-C: Clamping Structure and its Elements

FIGS. 2A-B illustrate an embodiment of a clamping structure 2000 comprising a plurality of elongate strips 2006 arranged in parallel or semi-parallel fashion. FIG. 2C is a photograph of an embodiment of a clamping structure 2000. In embodiments, the elongate strips may also be arranged in a non-parallel fashion. The various cells within this clamping structure 2000 may have a variety of shapes and sizes. As will be described in greater detail below, the length and shape of the elongate strips 2006, intervening members 2010, and cells 2004 may be designed so as to facilitate collapse and thus greater transformation of the clamping structure. In certain embodiments, the junctions 2900 between the elongate strips and intervening members may be thinned to better facilitate rotation and thus clamping of the clamping structures. In some embodiments, the clamping structure is tearable, such that the structure may be shaped into any desired size or shape. As described elsewhere in the specification, tears may be completed at the intersections between intervening members and elongate strips or at any suitable location along the elongate strip or intervening member.

All clamping structures described herein this section or elsewhere in the specification may be fashioned to be any size. However, to better accommodate the needs of the clinical environment, in certain embodiments, the clamping structures described herein may be provided in a pack of two sizes, one smaller clamping structure and one larger clamping structure about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The clamping structures within the pack may be of a variety of sizes in relation to one another such as the ratios described above.

In certain embodiments, the clamping structure 2000 can collapse in any manner described in this section or elsewhere in this specification with or without the application of negative pressure. For example, the clamping structure may collapse significantly more in one plane than in another plane upon application of negative pressure. In some embodiments, the clamping structure is configured to collapse more in a horizontal plane parallel to the length and width of the clamping structure than in a vertical plane perpendicular to the horizontal plane. In embodiments, a particular row of cells may collapse in a first direction, while another row may collapse in the same or an opposing direction. In certain embodiments, the clamping structure may collapse along the width of the clamping structure while remaining relatively rigid along the length and the height of the clamping structure. In certain embodiments, the clamping structure may also transform its overall shape while collapsing, for example, bending along its length or increasing curvature.

The clamping structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the clamping structure may comprise a radio opaque material, to more readily allow a clinician to find pieces of the clamping structure within the wound.

Returning to FIG. 2A, clamping structure 2000 may have a concave side 2101 and a convex side 2102, each extending the length of the clamping structure from a first end 2201 to a second end 2202, with the convex side opposite the concave side. The concave side 2101 and the convex side 2102 are defined by two outmost elongate strips. In some embodiments, as shown by FIGS. 2A-C, each of the concave side and the convex side may have a partial-elliptical shape. In certain embodiments, the concave side and the convex side are bent or curved in the same direction so that they are aligned in semi-parallel fashion. For example, as shown by FIGS. 2A-C, the concave side may be bent or curved concavely with respect to the clamping structure and the convex side may be bent or curved convexly with respect to the clamping structure. In embodiments, the concave side may be straight while the convex side is curved or bent. In certain embodiments, the concave side and the convex side may be bent or curved in opposite direction. The concave side and the convex side may taper toward the first and the second end. In some embodiments, the clamping structure may be at least partially crescent-shaped or half-elliptical-shaped. In some embodiments, the clamping structure may be symmetrical about the central transverse axis.

The clamping structure 2000 further may comprise a concave side wall 2301 defined by the concave side 2101 along the height of the clamping structure, and a convex side wall 2302 defined by the convex side 2102 along the height of the clamping structure. In some embodiments, both of the concave side wall and the convex side wall are parallel with the height and make up the right angle with regard to the horizontal plane. In other embodiments, either of the concave side wall and the convex side wall will be tilted with regard to the height. In some embodiments, the concave side wall and the convex side wall are straight along the height. In other embodiments, the concave side wall and the convex side wall may be curved along the height, so that the clamping structure can be more suitably applied to a contoured object.

As described above, the clamping structure 2000 may comprise a plurality of cells 2004 provided side-by-side, each cell defined by one or more walls, each cell having a top end and a bottom end with an opening extending through the top and bottom ends. As with the other clamping structures described herein this section and elsewhere in the specification, the clamping structure 2000 may be configured to collapse by collapsing one or more cells 2004. In some embodiments, the cells are all of the same approximate shape and size; however, in other embodiments, the cells are of different shapes and sizes.

The elongate strips 2006 may be made from one single material, such as those described elsewhere in the specification, or the elongate strips may be made from multiple materials. For example, elongate strips 2006 may comprise sections of more rigid material and sections of more flexible material. The elongate strips 2006 may be curved along their length so as to facilitate the curve of concave side and/or the convex side the clamping structure 2000. The elongate strips may be curved in the same direction with either the concave side, the convex side, or both. In some embodiments, each of the elongate strips may be curved in the same direction so that they are arranged in parallel or semi-parallel fashion. The arch of the curves of the elongate strips 2006 may vary considerably, with some strips 2006 being highly curved while others are minimally curved or even straight. In some embodiments, the clamping structure may have one elongate strip between the concave side and the convex side. In other embodiments, the clamping structure may have zero, two, three, four or more elongate strips between the concave side and the convex side.

Similarly, the clamping structure 2000 can further comprise a plurality of intervening members 2010 connected to the elongate strips 2006. The intervening members 2010 may all be of a similar shape and size or they may be of a variety of shapes and sizes. The intervening members may be constructed from any material disclosed herein this section or elsewhere in the specification. Further, the intervening members may be constructed from multiple materials.

The clamping structure 2000 and all clamping structures described in this section or elsewhere in this specification can collapse on a variety of timescales in a dynamic fashion. In certain embodiments, the majority of the collapse may occur within the first few minutes upon application of negative pressure. However, after the initial collapse, the clamping structure may continue to collapse at a much slower rate, thereby applying increasing longitudinal tension over a long period of time and drawing the first end and the second together.

In certain embodiments, up to 90% of the collapse of the clamping structure may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the clamping structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

FIG. 2B is an illustration of the top view of the clamping structure embodiment of FIG. 2A. In some embodiments, the pattern of the clamping structure 2000 is designed in such a way as to facilitate maximum collapse of the clamping structure. Preferably, maximum closure is in a direction perpendicular to the length of the elongate members and within the horizontal plane. As will be described in greater detail below, greater closure may be achieved by varying the length of the elongate strips 2006, the length of the intervening members 2010, and the shape of the cells 2004. The shape of the cells 2004 may comprise any shape described herein this section or elsewhere in the specification. For example, as depicted in FIG. 2A, the cells 2004 may be diamond-shaped or parallelepiped with smaller diamond-like shapes 2020 located within larger diamonds 2022. Such a construction may provide greater overall clamping of the clamping device 2000 to provide for maximum closure of the wound. Additionally, the smaller diamond-like shapes 2020 located within larger diamonds 2022 can spread the load over a greater area reducing the chance of damage to the tissue structures below the matrix. This construction can also reduce the likelihood of the foam or the drape being pulled into the matrix and preventing closure of the wound.

FIG. 2C is a photograph of an embodiment of an apparatus for use with negative pressure with the clamping structure 2000. Here, the clamping structure 2000 is contained within an air-tight plastic bag. However, in embodiments, the apparatus may contain other means of forming an air-tight seal to maintain the negative pressure environment around the clamping structure. For example, a drape such as described in this section or elsewhere in the specification may be used with the clamping structure to maintain the negative pressure.

Any of the clamping structures described herein this section or elsewhere in the specification may be constructed by any suitable means. For example, the clamping structures may be constructed via molding or may be printed directly using 3D printing technology. In certain embodiments, the clamping structures of FIGS. 2A-C may be constructed from a single polymer via 3D printing. In some embodiments, the clamping structures may be constructed from a single polymer, two different polymers, three different polymers, or more than three different polymers. The clamping structures may be constructed from any material disclosed herein this section or elsewhere in the specification. The clamping structure can be made by cutting the structure out of a solid block of material. Methods used for cutting can include, for example, water jet cutting, laser cutting, or die cutting. The clamping structures may be cut to size along the walls of the cells 2004. For example, the intervening members along the outside face of elongate strips 2006 can be cut off to appropriately size the clamping structure. The clamping structure may be cut along the walls, along any portions of the elongate strips, and/or along any portions of the intervening members. In certain embodiments, the clamping structure may be created from a mold.

In some embodiments, the clamping structure 2000 of FIGS. 2A-C can be configured to include perforations or detachable sections that allow portions of the device to separate from the remainder of the device. For example, perforations may be incorporated into the joints 2900 between various cells 2004 contained within the clamping structure 2000, allowing for the removal of individual rows or cells to alter the shape of the clamping structure 2000.

In some embodiments, the clamping structure 2000 of FIGS. 2A-C may have holes or notches on the elongate strips 2006 and/or intervening members 2010 defining cells 2004, such that cells are in fluidic communication with each other. This feature may act as fluid pathways for drainage of wound fluid while helping propagation of negative pressure along the clamping structure, thus facilitate collapsing of the clamping structure 2000.

Applicable to all clamping structures or wound closure devices described in this section or elsewhere in the specification, the clamping structure or wound closure device may be tearable such that the clamping structure may be shaped into any desirable shape. In some embodiments, the clamping structure may be torn at the intersections between intervening members and elongate strips, while in further embodiments, the elongate strips or intervening members may be torn at any suitable position.

FIGS. 3A-4C: Design and Operation of Clamping Structure

Figure 3A:
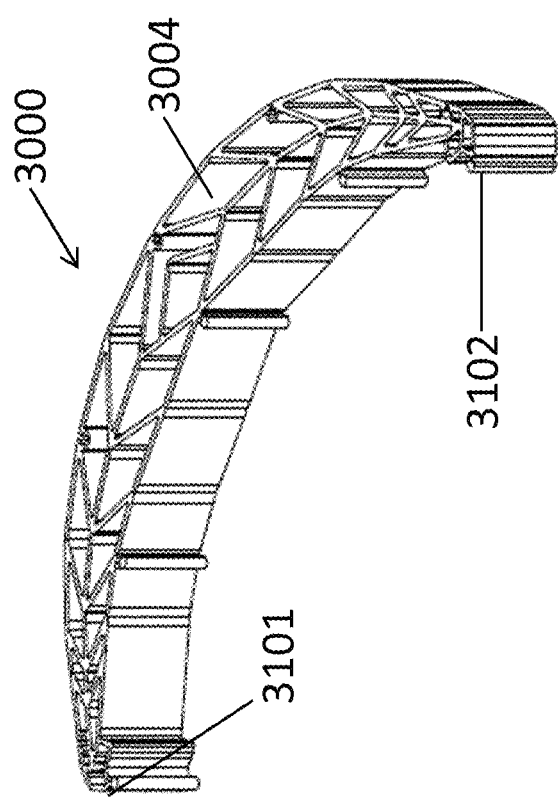
Figure 3B:
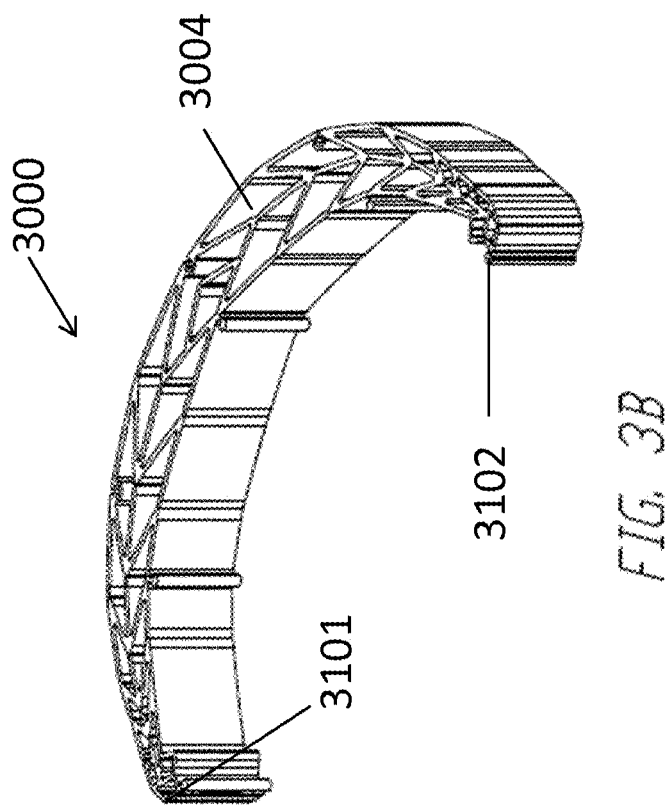

FIGS. 3A-4C illustrate an embodiment of a clamping structure 3000 having a cell configuration as described above. FIGS. 3A-C illustrate perspective views of the transformation of an embodiment of the clamping structure 3000 before, during and after collapse with or without negative pressure, respectively. In some embodiments, as shown by FIGS. 3A-C, when cells 3004 collapse with or without negative pressure, the curvature of the elongate strips of the clamping structure increases and the distance between first end 3101 and the second end 3102 decreases. In some embodiments, the first end and the second end completely touches each other upon the collapse of the clamping structure. In embodiments, the distance between the first end and the second end after collapse is less than about: 90%, 80%, 70%, 60%, 50%, 40%, 30%, 20%, or 10% of the original distance between the first end and the second end. In certain embodiments, the distance between the first end and the second end may be approximately 0% of the original distance, and the first and second ends may be touching or narrowly not touching.

Figure 3D:
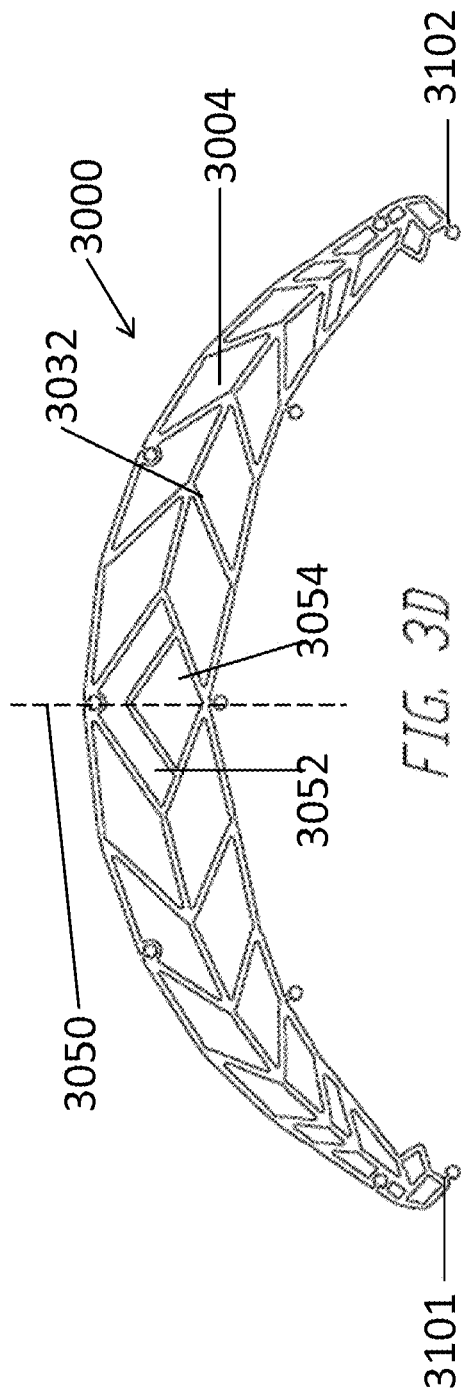
Figure 3E:
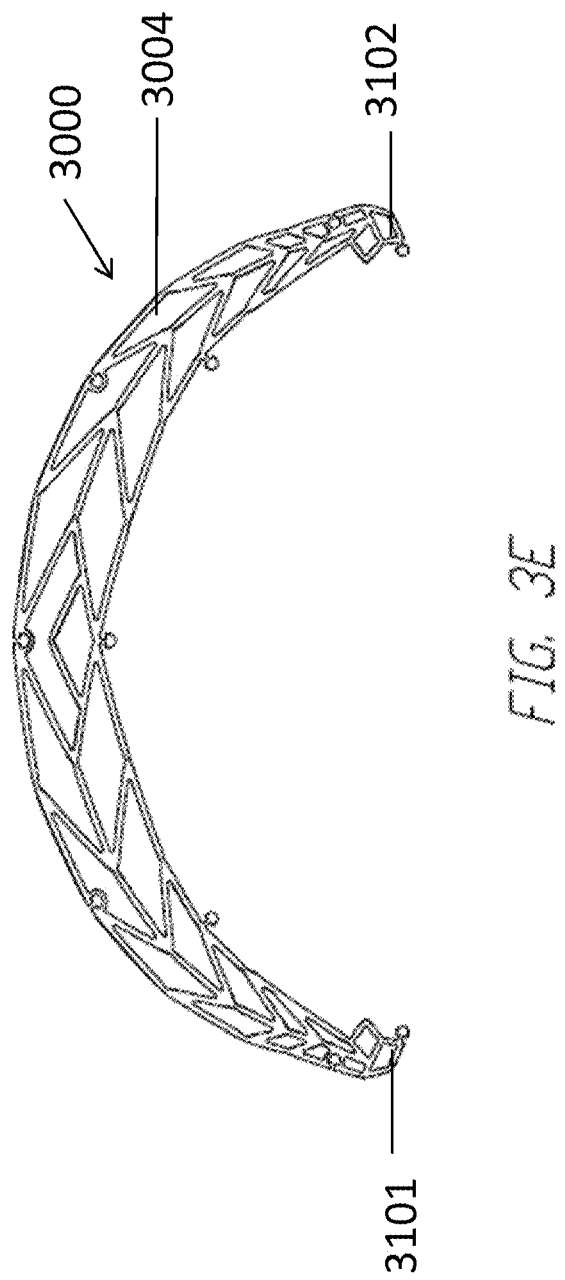
Figure 3G:
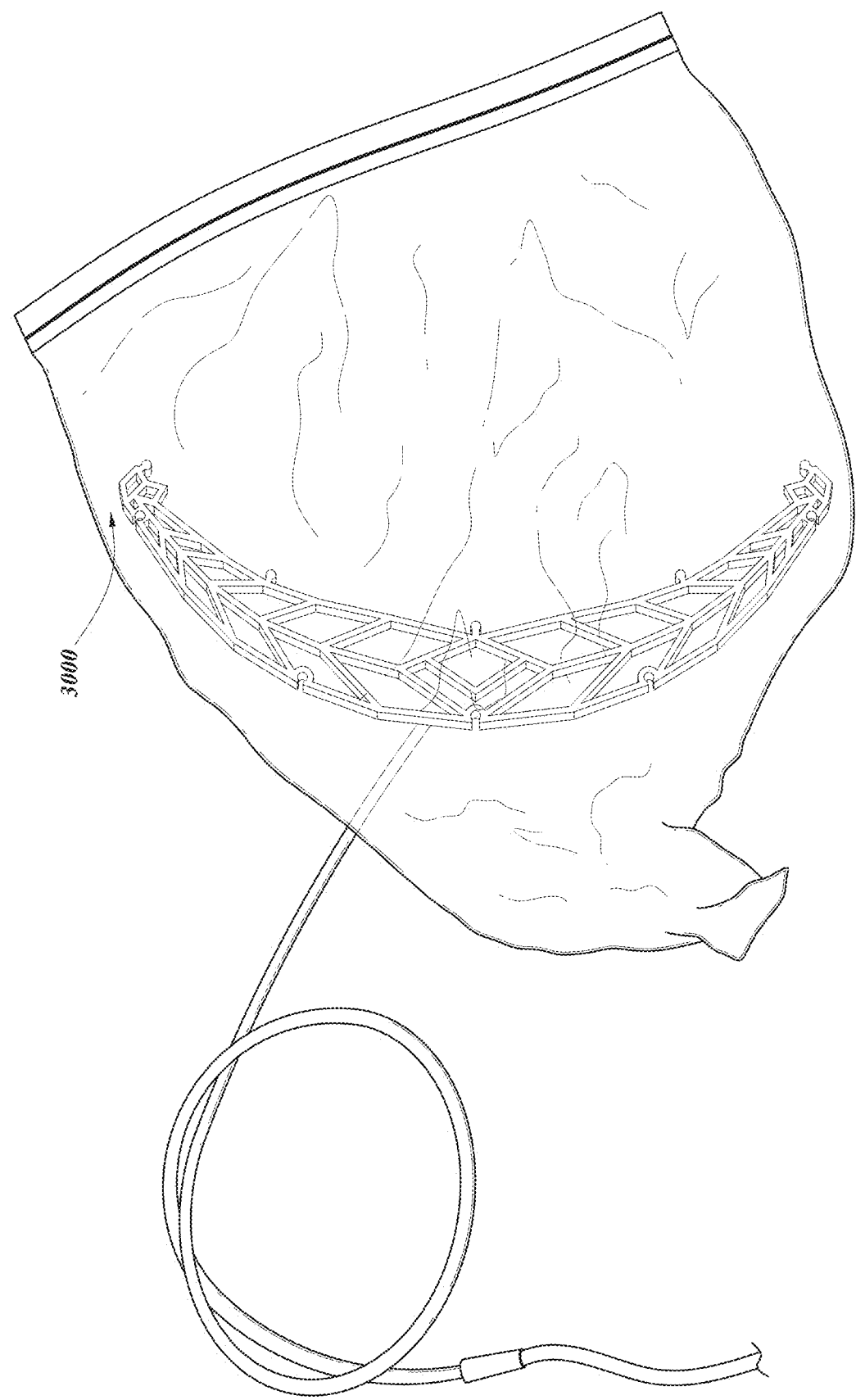
FIGS. 3G-H depict an embodiment of an apparatus for use with negative pressure having a clamping structure in a natural state and a collapsed state.
Figure 3H:
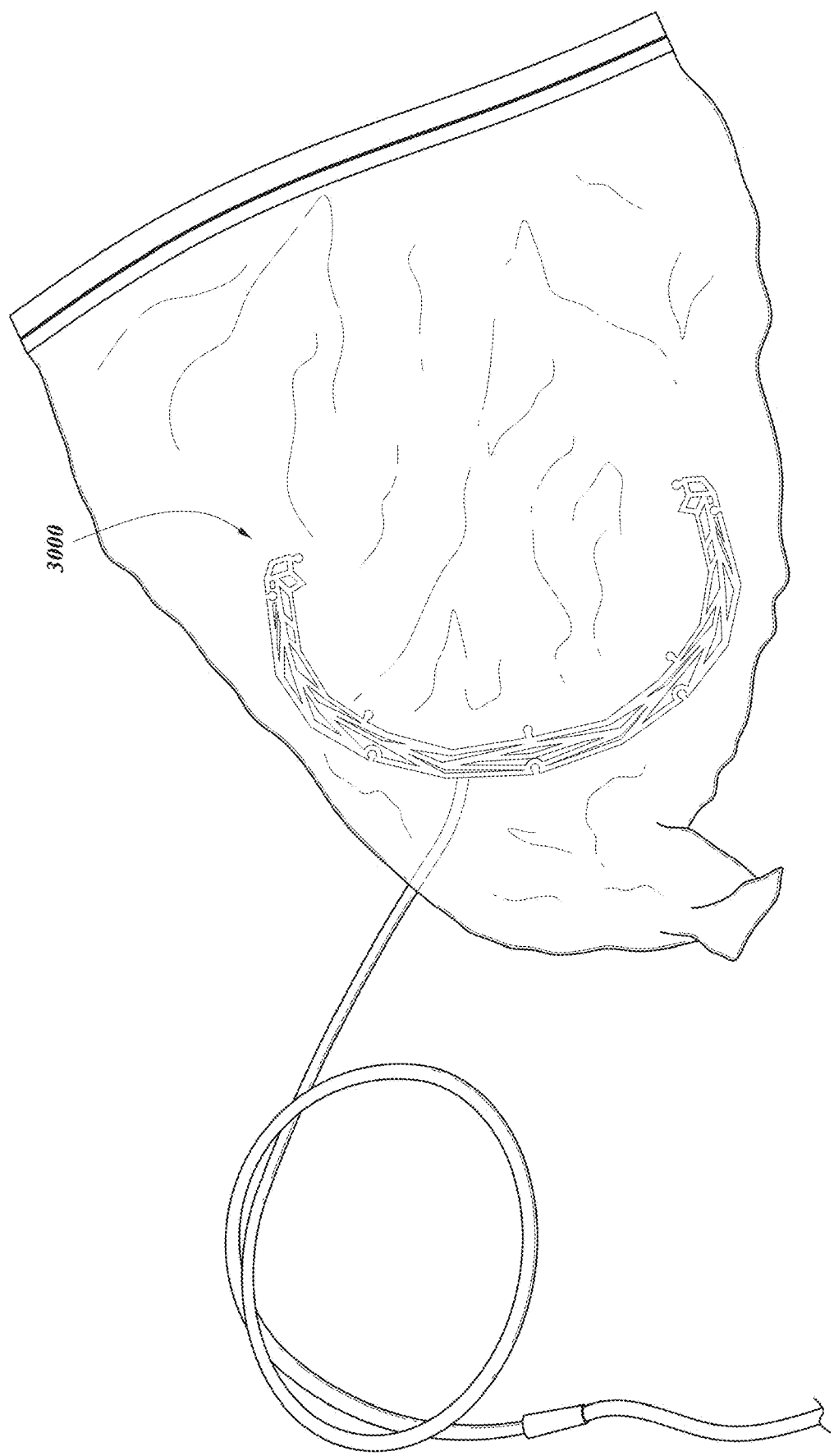

To facilitate various types and degree of clamping (for example, maximum clamping) the shape, size, and location of the elongate strips, intervening members, and cells may be determined via various suitable methods. FIGS. 3D-F illustrate a top view of the embodiment of FIGS. 3A-C. For example, as depicted in FIG. 3D, each collapsible cell 3004 may have four sides, and each intersection between an intervening member(s) and/or elongated strip(s) may be modeled via pin-joints 3032. As depicted in FIGS. 3A-F, the clamping structure 3000 may collapse from an open state to a semi-collapsed state, and to a fully collapsed state. In some scenarios, further collapse down to the embodiment depicted by FIGS. 3C and 3F may be desirable to maximize clamping by drawing the first end and the second end of the clamping structure close together as possible. FIGS. 3G-H depicts an embodiment of clamping structure 3000 before and after negative pressure is applied.

As illustrated in FIG. 3D, in certain embodiments, the process of determining the optimal shape, size, and location of the elongate strips, intervening members, and cells for wound closure may be facilitated by constructing the clamping structure in a mirrored pattern with opposite sides of a mirror line 3050 (which may also be referred to as the transverse axis, perpendicular to a length of the clamping structure), thereby making the curve and collapse of the clamping structure symmetrical. The mirror line may be located in any suitable location within the clamping structure, such as diagonally across the clamping structure. In certain embodiments, this method may lead to large diamond-shaped cells near the center line. These large diamond-shaped structures 3052 may be further subdivided to further support the clamping structure by including smaller diamond shapes 3054 within larger shapes. In some embodiments, these smaller shapes 3054 within a larger shape 3052 may comprise any shape disclosed herein this section or elsewhere in the specification. The larger cells may be further subdivided by two smaller shapes, three smaller shapes, four smaller shapes, or more than four smaller shapes. In some embodiments, the clamping structure may contain multiple mirror lines, thereby having multiple subsections that are symmetrical or different.

Figure 4A:
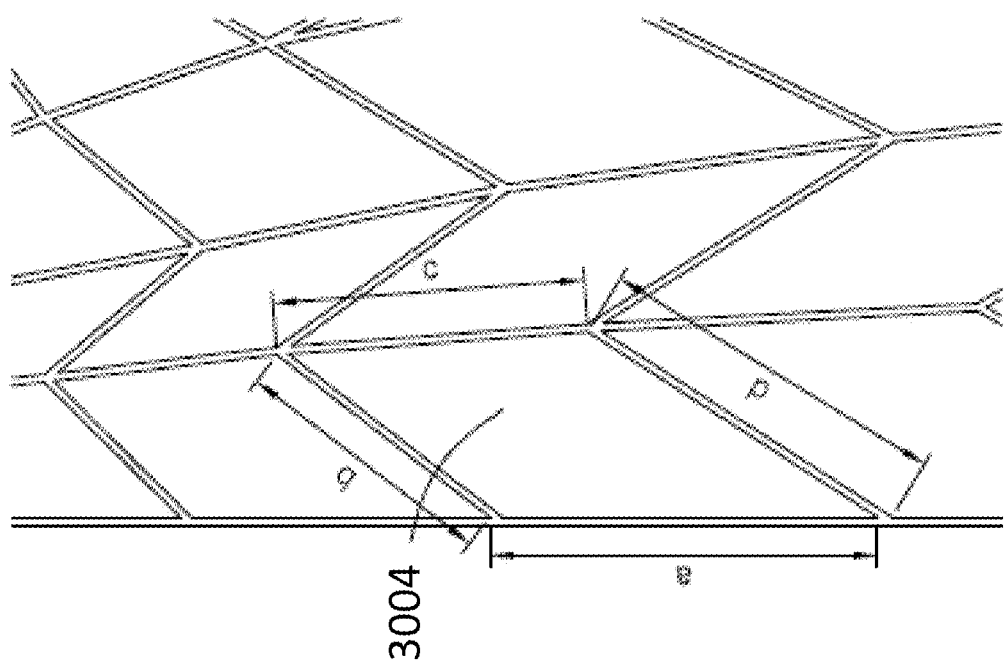
FIGS. 4A-C illustrate cell configurations of an embodiment of a clamping structure.

As illustrated in FIG. 4A, for a four-sided cell to collapse, it must follow a simple formula: $a+b=c+d$, where a, b, c, and d are the lengths of individual sides of a single cell within the clamping structure such as the cell 3004 of FIG. 3G. When members c and b collapse together, then d and a collapse together. Such a formula may be the basis for developing a pattern for a clamping structure that maximizes collapsibility.

Figure 4B:
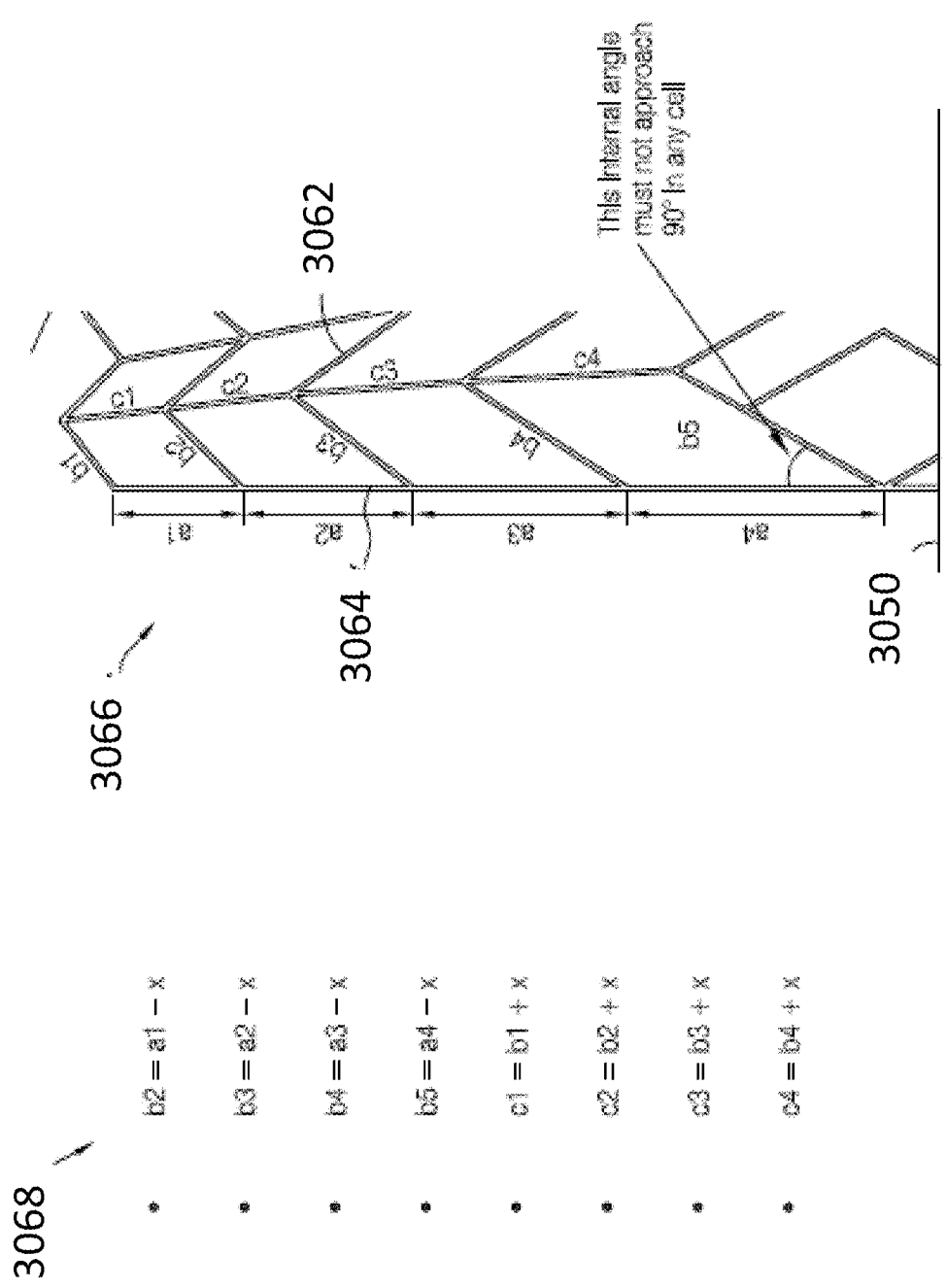
Figure 4C:
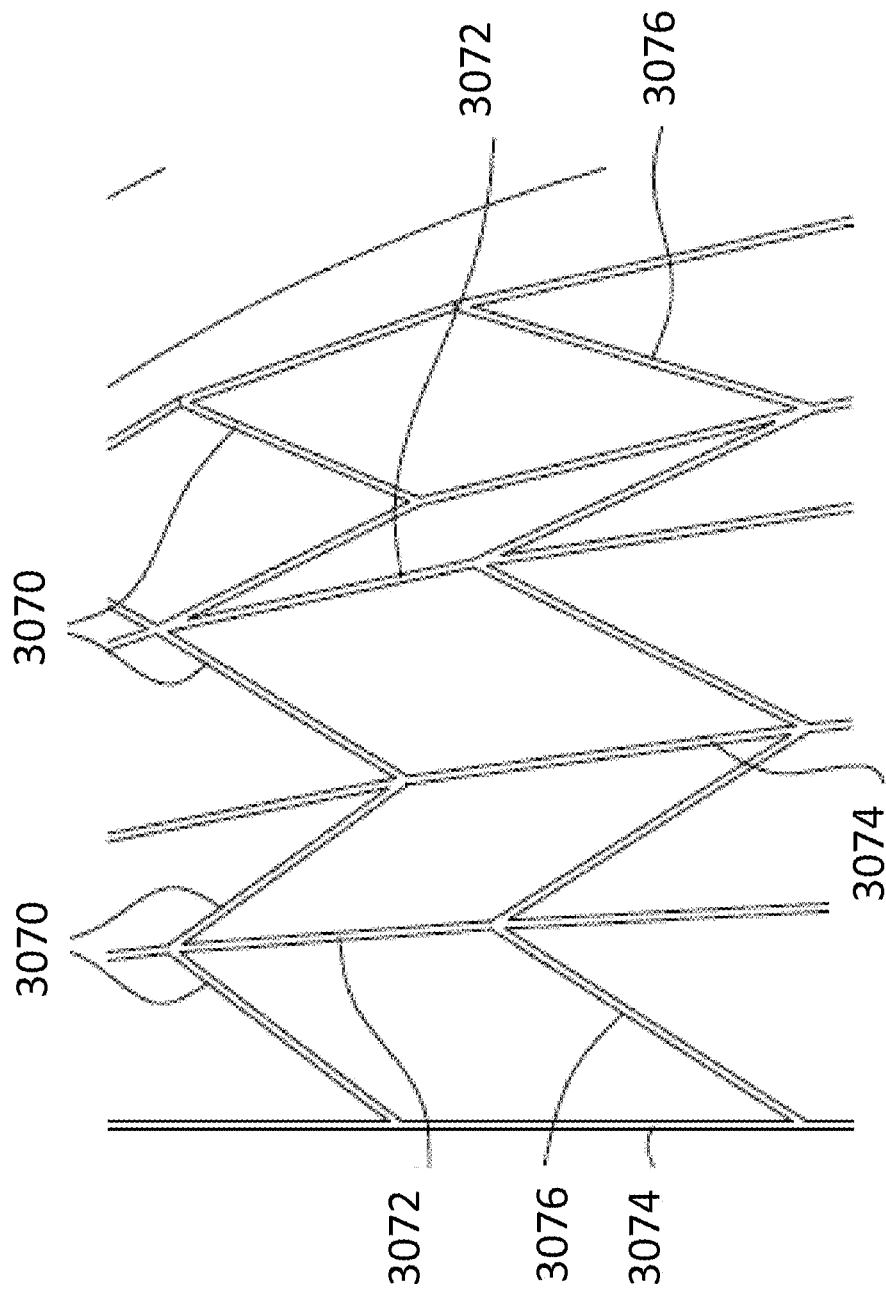

Further, as illustrated in FIG. 4B, the elongate strip side of cells were progressively lengthened ($a4>a3>a2>a1$) towards the horizontal mirror line 3050, thereby achieving a curve in the clamping structure while preventing any of the intervening members 3062 from becoming perpendicular to the elongate strips 3064 (i.e. having an internal angle of 90 degrees). As illustrated in FIG. 4B, a value for b1 may be chosen, at which point an arbitrary offset value x may also be chosen to ease the construction of the various cell geometries. Using the progressive values for a1 through a4, illustrated visually in FIG. 3H 3066, values for b1-b4 may be calculated 3068. Using calculated values derived from equations 3068 for the various walls of the individual cells allows for the design of a clamping structure that collapses completely, such as those depicted in FIGS. 3A-F.

In some embodiments, a method for generating a clamping structure design may include steps to speed up the initial geometry construction. For example, if all members from left to right in a specific row, as visualized by intervening members 3076 in FIG. 4C, a pattern then emerges where alternating vertical members are also the same length. Walls of the same length are indicated by their respective labels 3070, 3072, 3074, and 3076. Once the initial design is generated then individual cells may be modified by lengthening, shortening, removing or inserted according to the formulas of FIG. 4B to achieve the desired shape of the overall clamping structure.

FIGS. 5A-7B: Detachable Segments

Figure 5A:
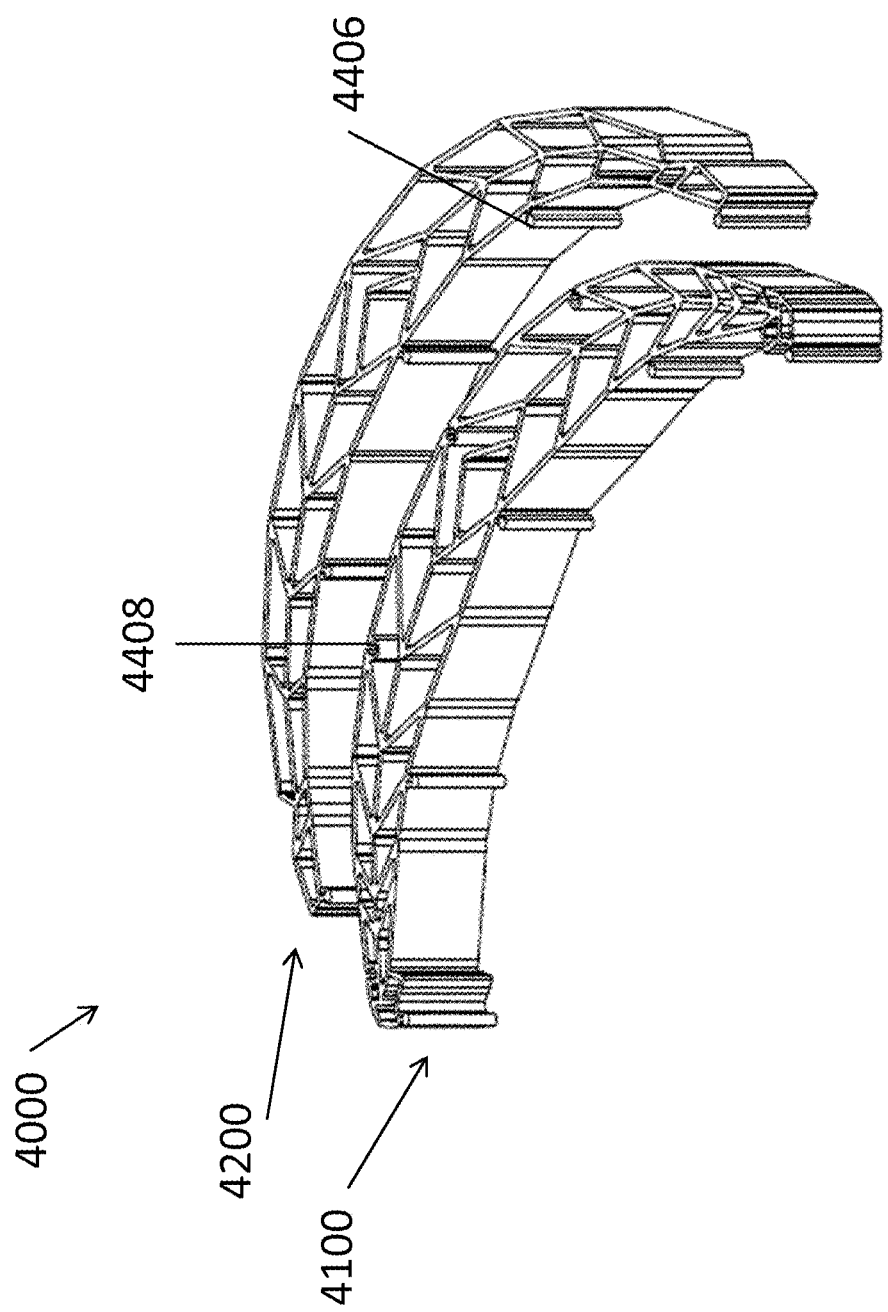
Figure 5B:
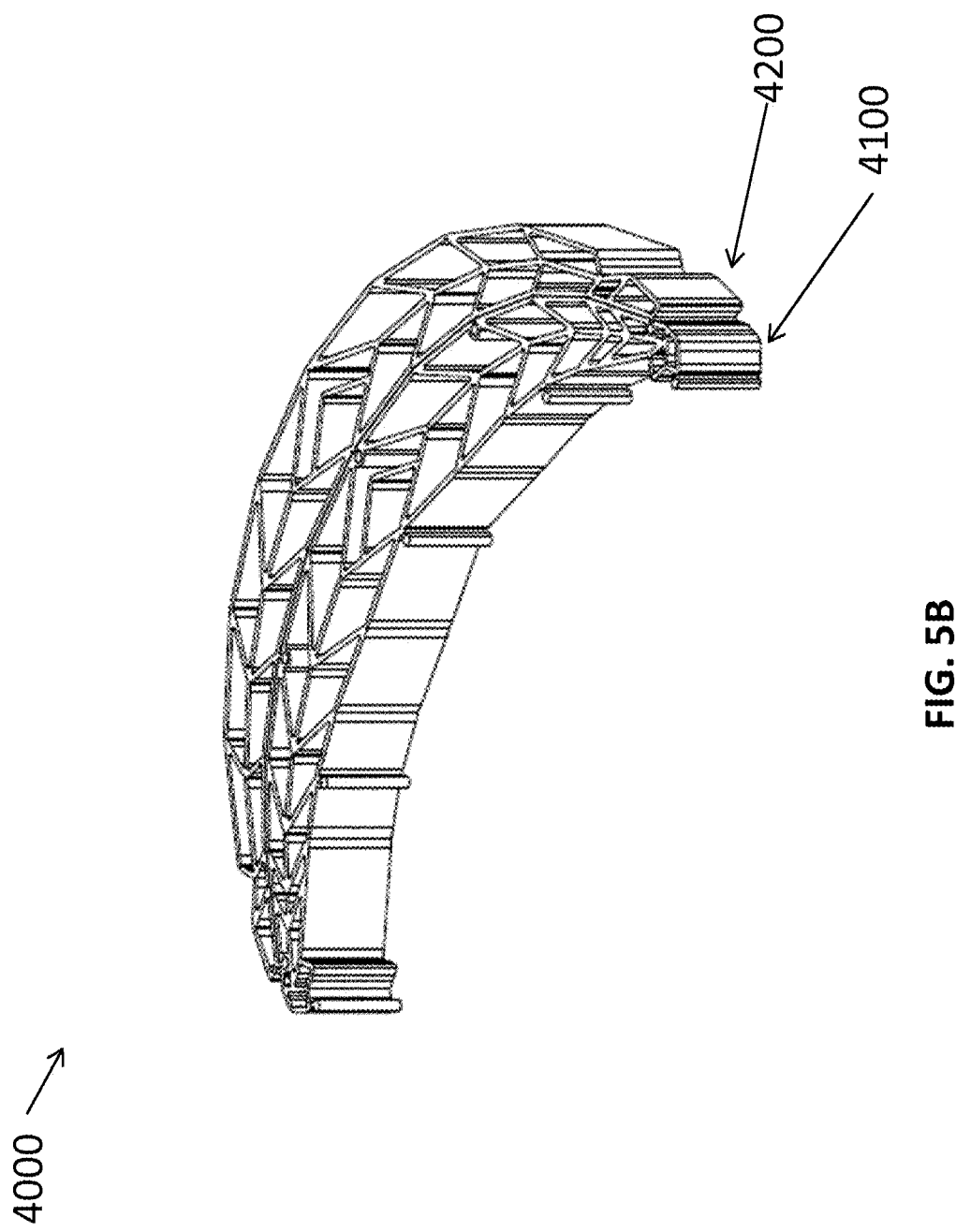

FIGS. 5A-B illustrate an embodiment of a clamping structure 4000, similar to the clamping structures disclosed previously in FIGS. 2A-2C, 3A-B, and 4A-C. Here, clamping structure 4000 comprises inner segment 4100 and a detachable segment 4200. In some embodiments, the detachable segment 4200 at least partially surrounds the inner segment 4100. In some embodiments, each of the segments may have a crescent shape. To adjust the clamping structure to desired shape or size, in embodiments, the detachable segment of the clamping structure 4200 may be removed from the overall structure to form a smaller clamping structure such as the inner segment 4100. In certain embodiments, there may be at least: one, two, three, four, five, six, seven, eight, nine or ten removable segments.

One of skill in the art will understand that the detachable sections of the clamping structures of FIGS. 5A-7B, and any detachable clamping structure and/or wound closure device disclosed herein this section or elsewhere in the specification, may be removed in any suitable direction. For example, the clamping structure may be configured such that the detachable section(s) may be removed horizontally within an x-y plane parallel to the longest dimension of the clamping structure. In certain embodiments, the clamping structure may be configured such that detachable sections may be removed in a vertical direction in the z axis, perpendicular to the x-y plane. The clamping structure may have at least one detachable section removable in a horizontal direction and one section removable in a vertical direction. The detachable section(s) may be attached to the clamping structure in such a manner that the detachable section(s) may only be removed in a single direction, such as by the use of slots and/or channels as the attachment and receiving elements.

In embodiments, the clamping structure segments may be cut from the clamping structure 4000 to produce a smaller structure. In certain embodiments, the clamping structure may have pre-cuts along the shape of the segments 4100 and 4200 to allow the segments to be tearable and easily removed by hand from the clamping structure. The detachable segments may be adhered to the remainder of the clamping structure via adhesive, Velcro®, or other suitable adhesive means. In certain embodiments, the removable sections may be held together by the tightness of the structures squeezing together and/or via friction. In some embodiments, magnets and/or suction cups may be used to keep the segments together.

Figure 5D:
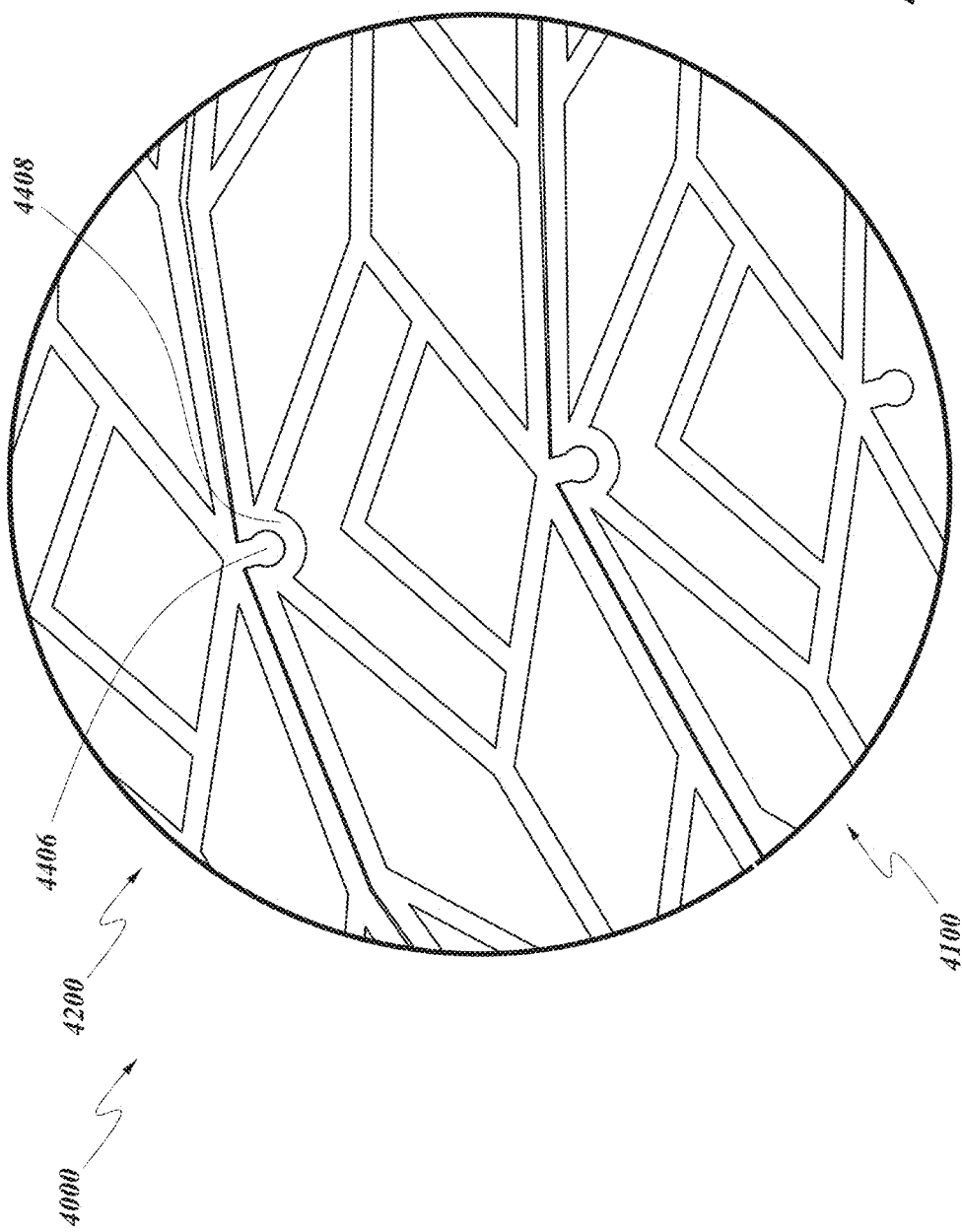

As shown in FIGS. 5A-D, in some embodiments, detachable segments 4200 may comprise one or more attachment elements 4406, which may be in the form of prongs, hooks, tongues, screws, nails, or other suitable attachment means. FIGS. 5C-D are photographs of such embodiments. As shown in FIG. 5C-D, the attachment elements 4406 attach to receiving elements 4408 of the inner segment 4100 which may be in the form of grooves, holes, windows, or any suitable means. For example, FIG. 5C-D depicts an embodiment of a clamping structure 4000 where the attachment elements 4406 are tongues which fit into the receiving elements, which are grooves 4408. The attachment elements may serve to maintain attachment of the detachable segment to the inner segment or another detachable segment until the clamping element is re-sized by applying suitable force to separate the attachment elements from the receiving elements. In certain embodiments, detachable segments 4200 and inner segment 4100 may comprise both attachment elements 4406 and receiving elements 4408. For example, a detachable segment 4100 may comprise attachment elements 4406 on one side and receiving elements 4408 on the opposite side to allow the detachable elements 4200 to be stacked one after another. In certain embodiments, segments 4200 may comprise at least about 1, 2, 3, 4, 5, 6, 7, 8, 10, 15, 20, 30, or more than 30 attachment elements. In some embodiments, segments 4200 may comprise at least about 1, 2, 3, 4, 5, 6, 7, 8, 10, 15, 20, 30, or more than 30 receiving elements.

Figure 5E:
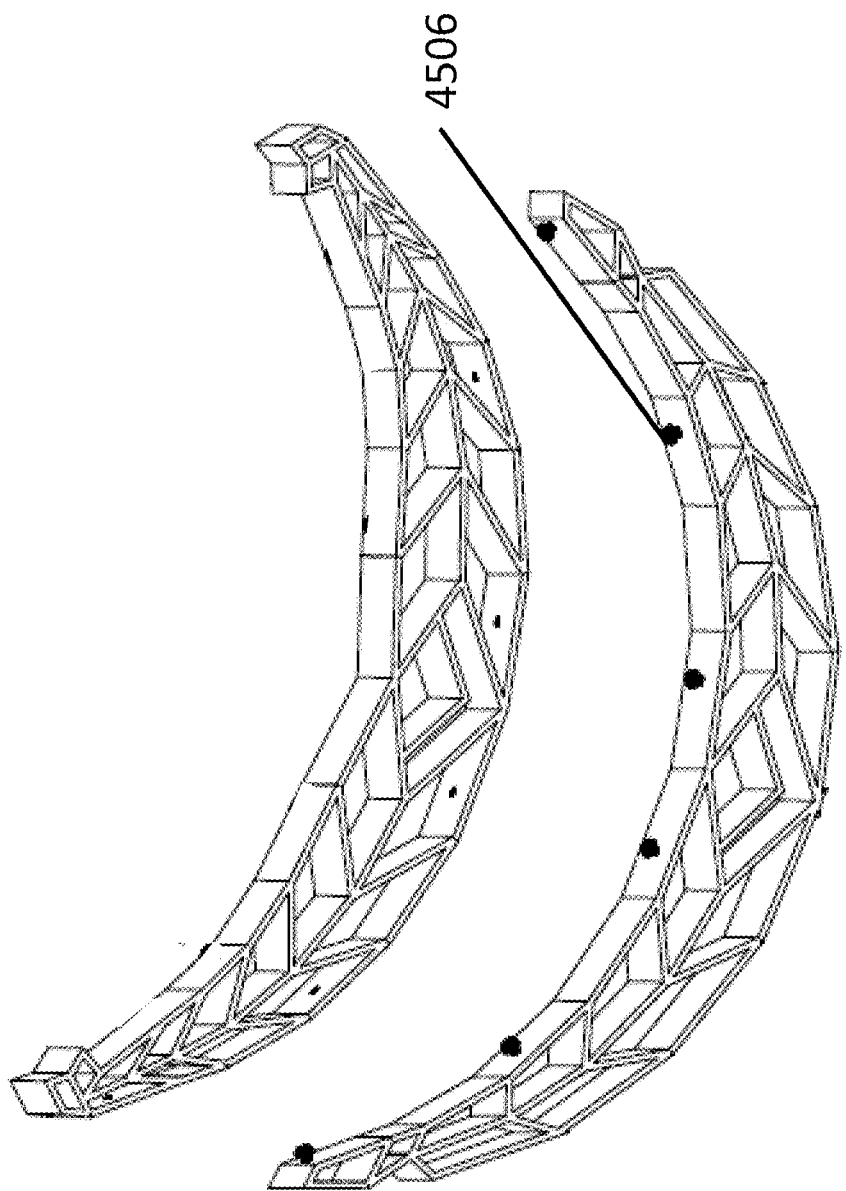
Figure 5F:
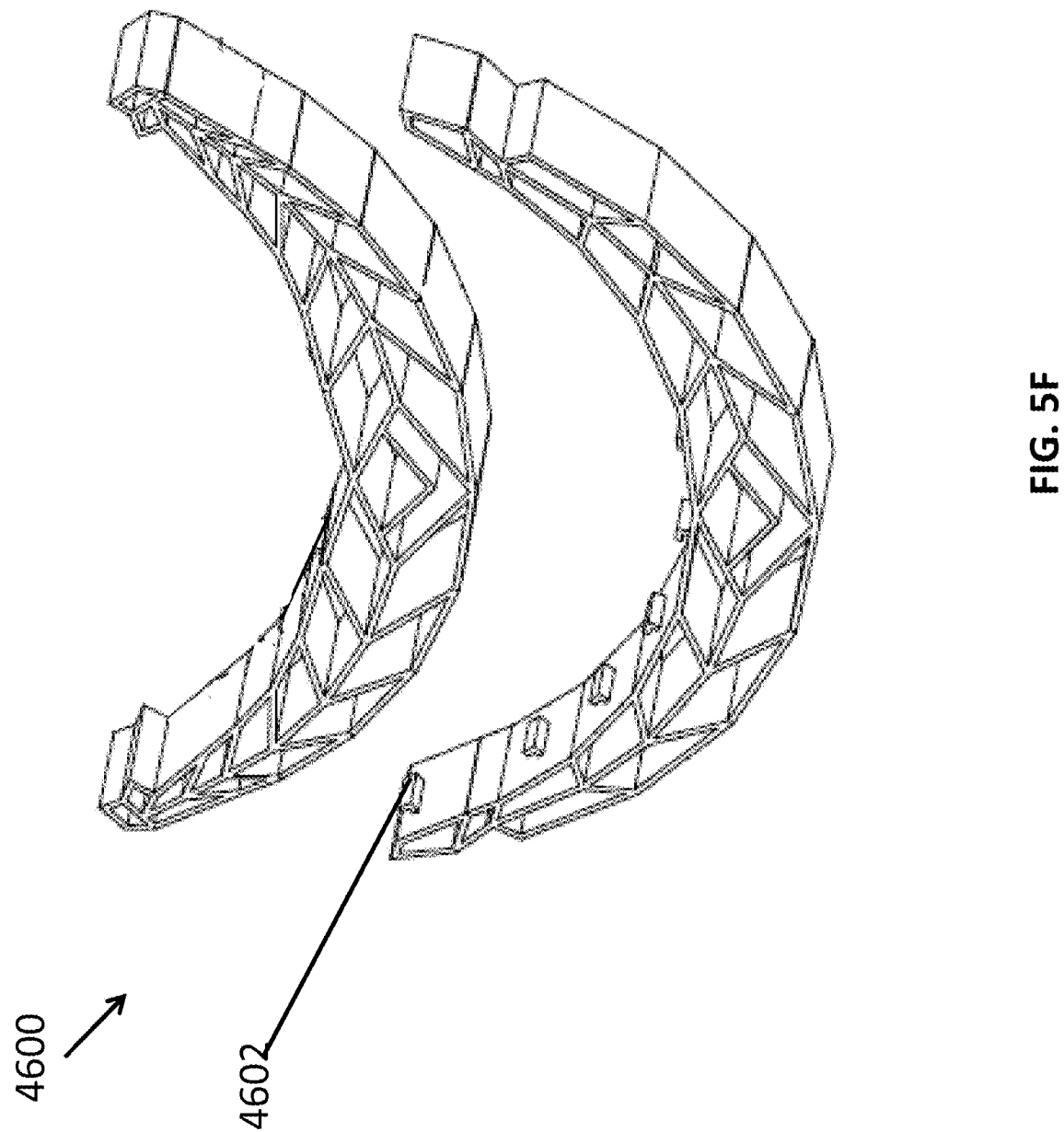
Figure 5G:
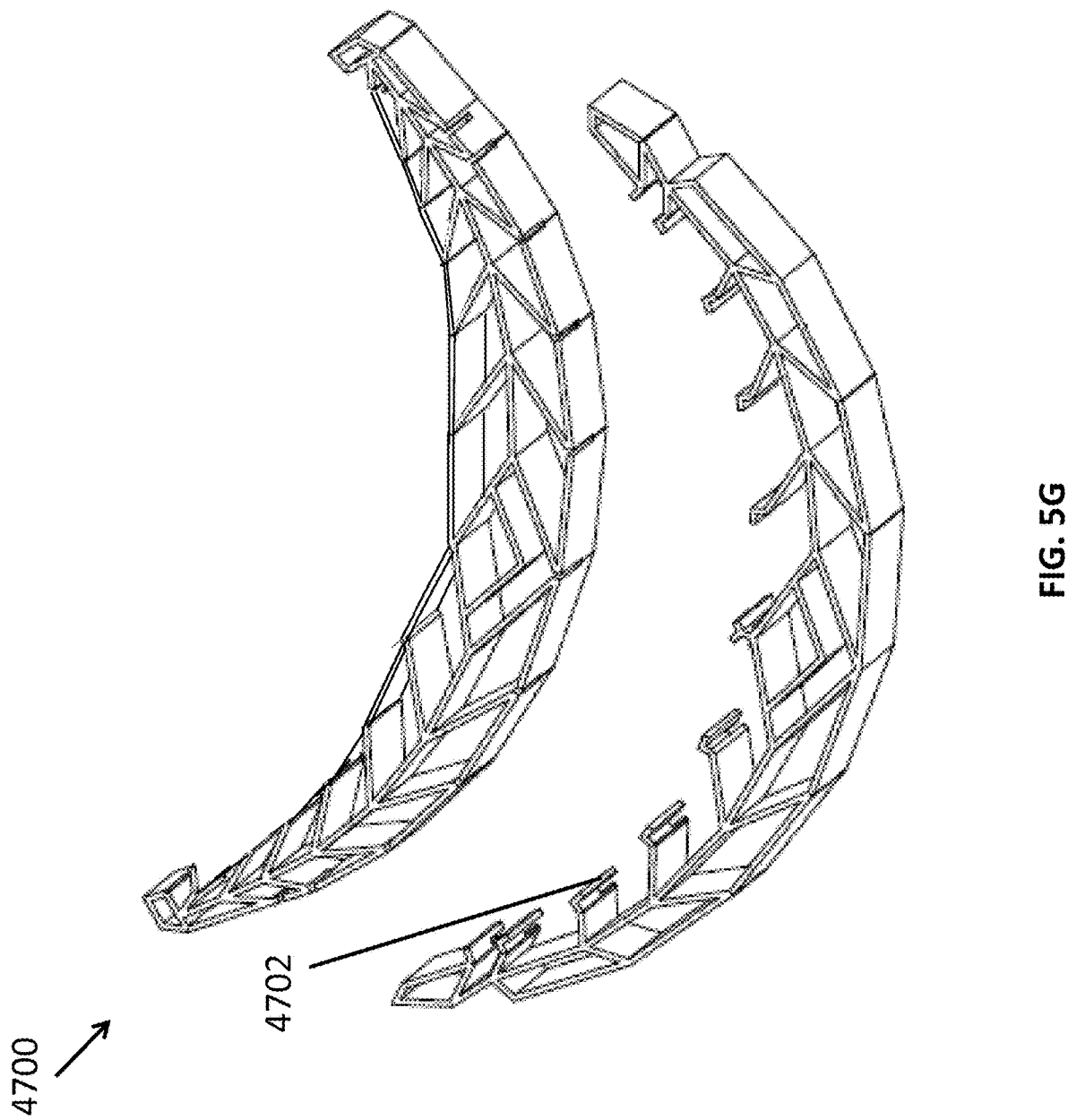
Figure 5H:
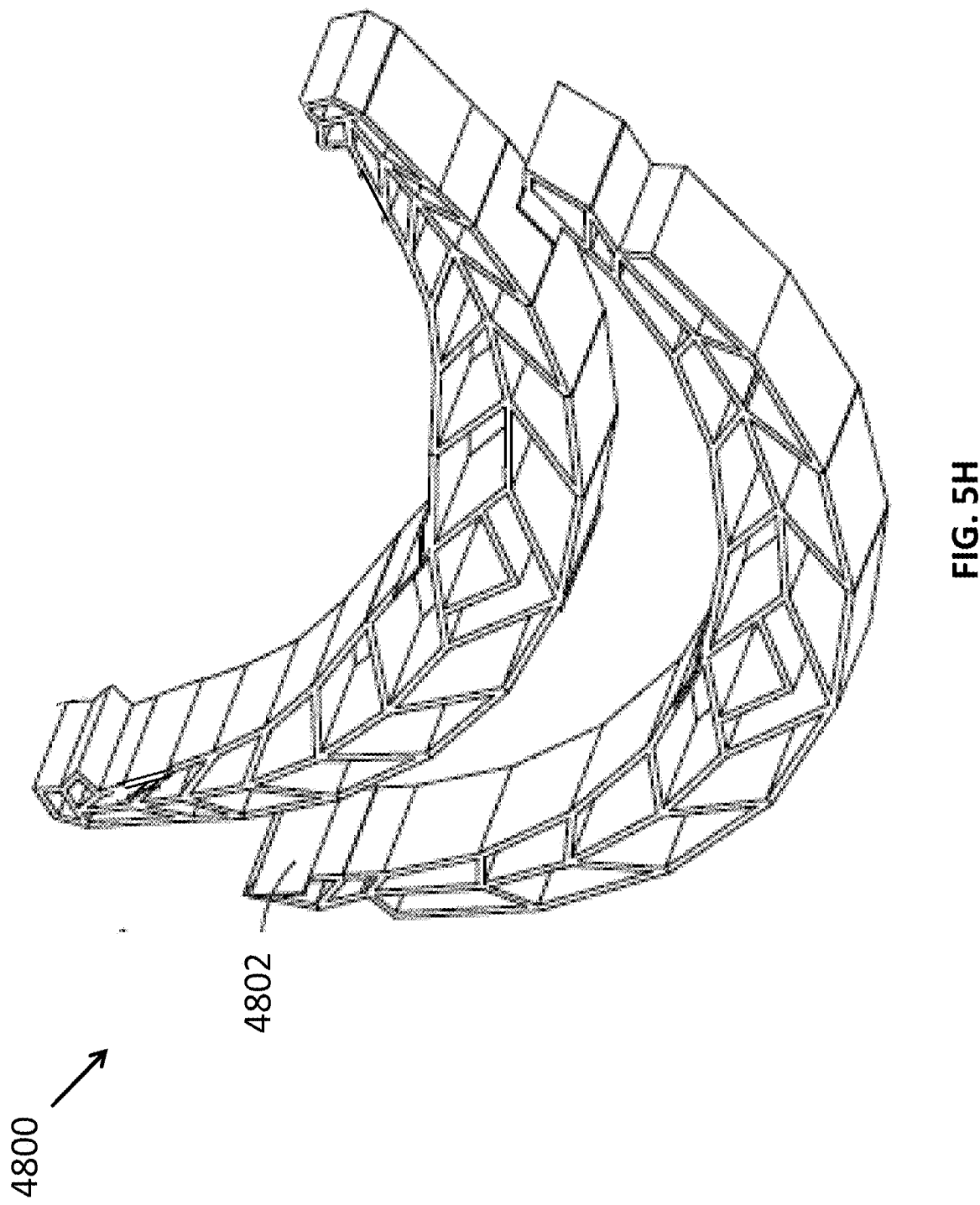
Figure 51:
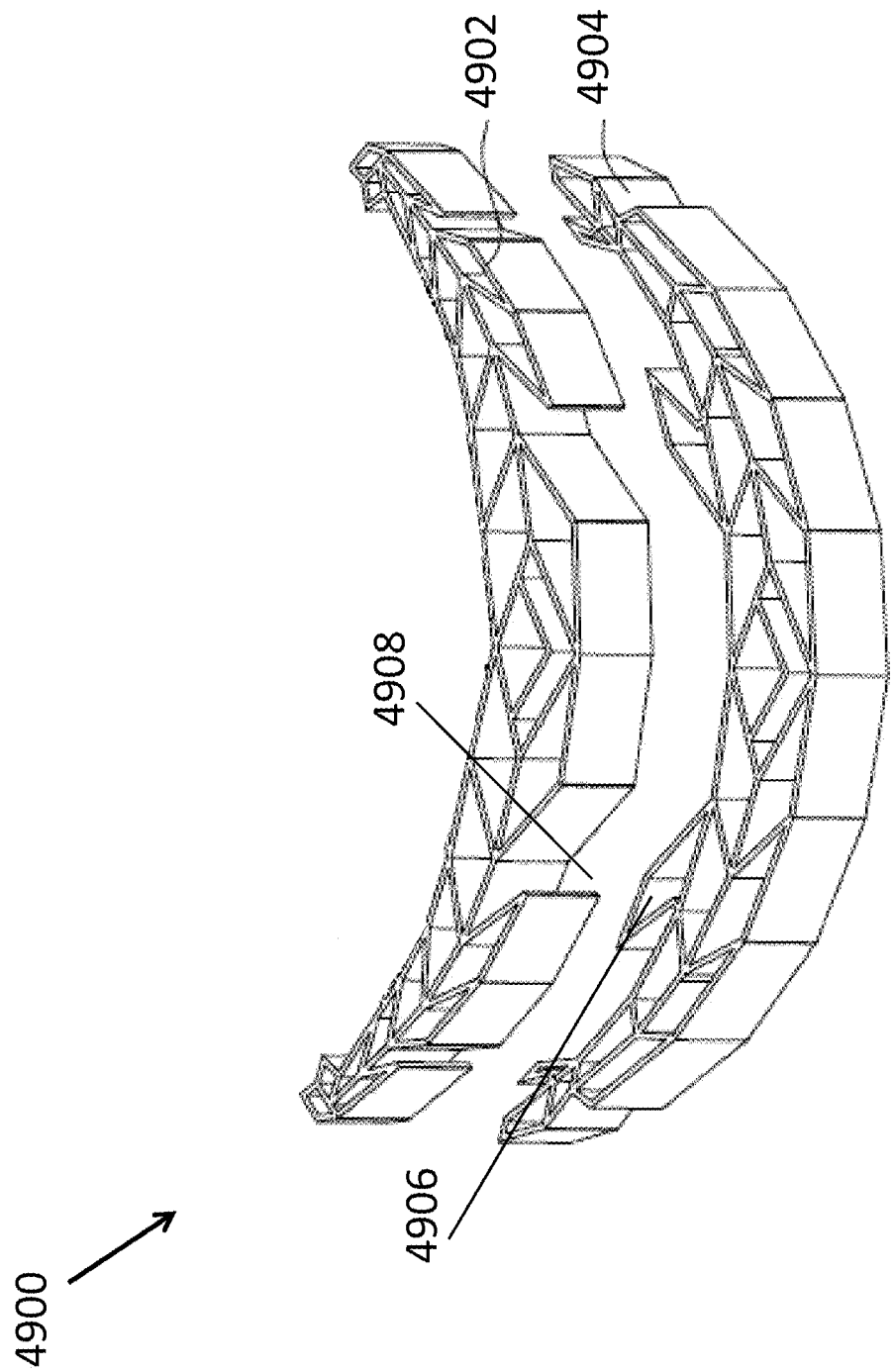

FIG. 5E depicts an embodiment of a clamping structure 4500 where the attachment elements 4506 are prongs. FIG. 5F depicts an embodiment of a clamping structure 4600 where the attachment elements 4602 are claws which fit into the receiving elements, which are grooves 4604. FIG. 5G depicts an embodiment of a clamping structure 4700 where the attachment elements 4702 are hooked and the receiving elements are configured to receive the hooks. FIG. 5H depicts an embodiment of a clamping structure 4800 where adhesive 4802 may be applied to certain areas of the detachable segments for adhesion to the outer surfaces of other detachable segments or the inner segment. Adhesive may also be applied to the inner segment.

FIG. 5I depicts a clamping structure 4900 similar to the clamping structures of FIGS. 5A-5H. Here the detachable segments 4904 comprise extended cells 4906 which fit into recesses 4908 of inner segment 4902 or another detachable segment 4904. In embodiments, the extended cells 4906 are configured to snap fit into the recesses 4908, such that the different segments can be separated from one another by the application of force. For example, separation can occur by the application of force by a user.

In certain embodiments, the detachable segments such as those disclosed above in relation to FIGS. 5A-I may be packaged within a separate kit from the clamping structure. The separately packaged detachable segments may comprise attachment elements and/or receiving elements such as those disclosed herein this section or elsewhere in the specification. Such separately packaged detachable segments may then be added to main clamping structure to increase the size and/or alter the shape of the clamping structure. In certain embodiments, the separate kit(s) of detachable segments may contain one detachable segment, two detachable segments, three detachable segments, four detachable segments, five detachable segments, or more than five detachable segments. In some embodiments, the detachable segments may be in the form of a crescent.

In certain embodiments, clamping structures, such as disclosed herein this section or elsewhere in the specification, may collapse in a different manner depending on the shape of the clamping structure. For example, in some embodiments, when the curvature of a clamping structure increases upon collapse of a cell or cells, such transformation may be greater when the difference between the length of the concave side and the convex side is greater. The difference between the length of the concave side and the convex side may be adjusted with installation or removal of detachable segments. For example, in FIGS. 5A-B, the difference between the length of the concave side and the convex side is greater in the clamping structure 4000 than in the inner segment 4100.

Figure 6A:
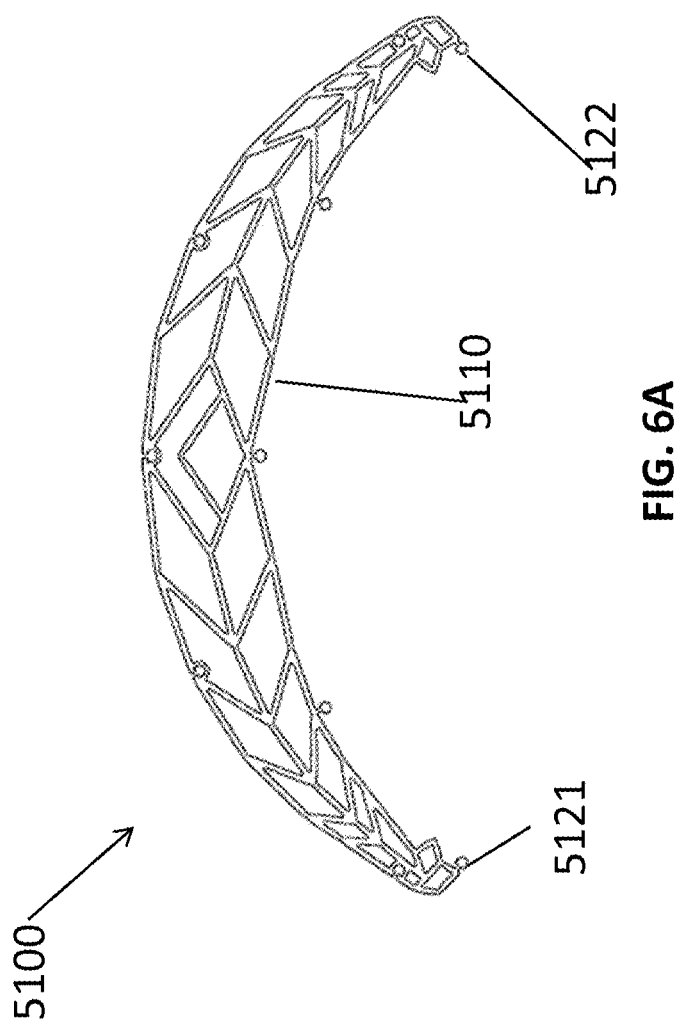
Figure 7A:
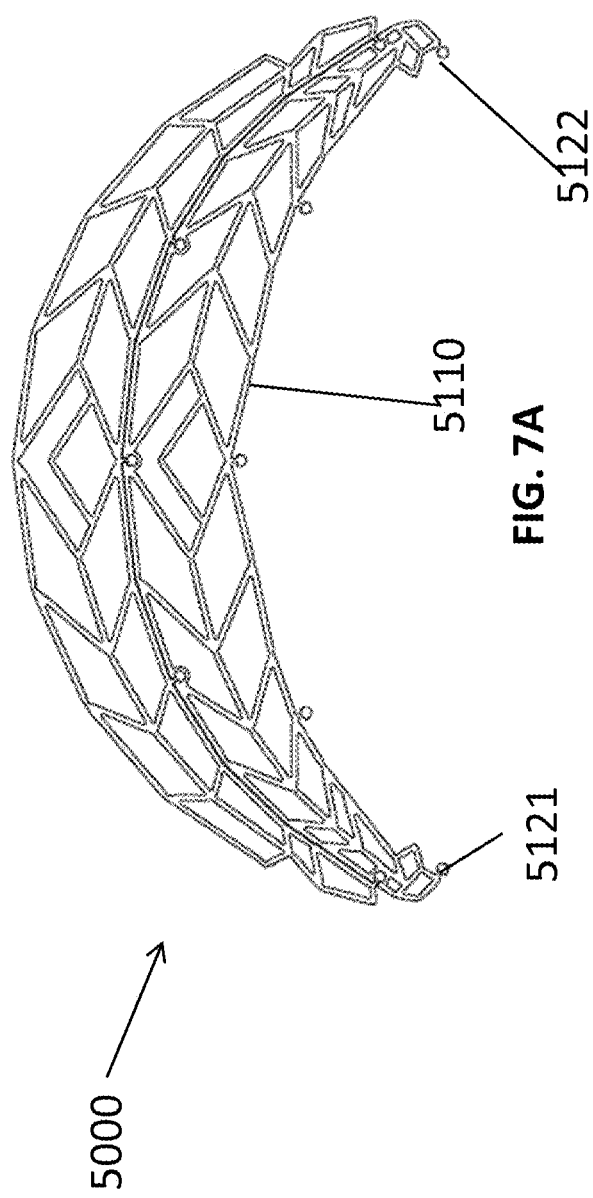
Figure 7C:
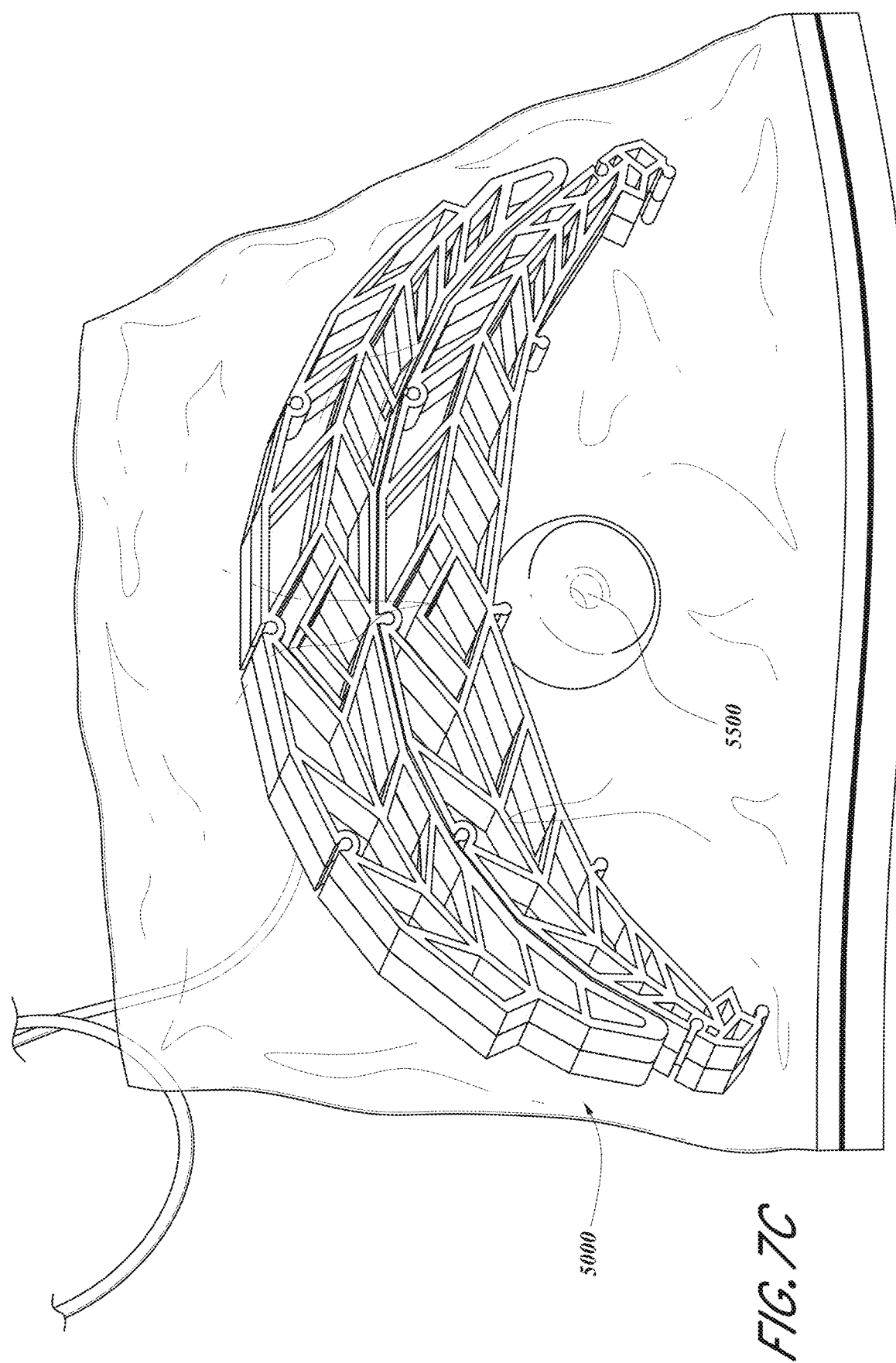
Figure 7D:
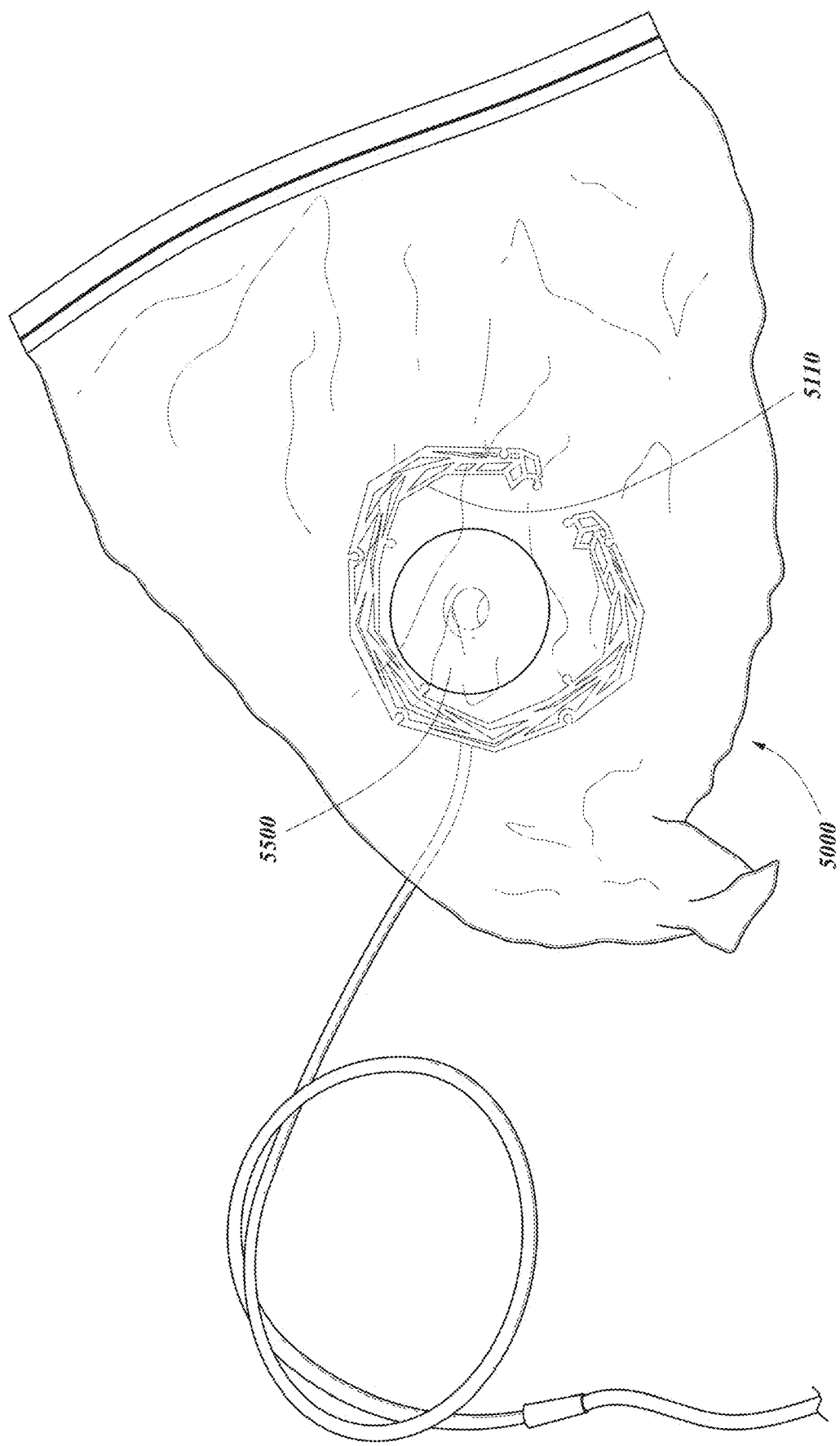

FIGS. 6A-7B compares the clamping of an embodiment of the clamping structure 5000 and the inner segment 5100 without the detachable segment 5200. Before collapse, the curvature of the concave side 5110 and the distance between the first end 5121 and the second end 5122 is identical as shown in FIGS. 6A and 7A. However, after collapse, the clamping structure with the detachable segment installed which is illustrated in FIG. 7B shows greater degree of transformation than the clamping structure without detachable segment which is illustrated in FIG. 6B. Photographs of such embodiment are shown in FIGS. 7C-D. Here, an embodiment of object 5500 subject to clamping of 5000 is shown. Here, the concave side 5110 of the clamping structure 5000 in FIG. 7D would form a relatively more intimate contact with the contoured object with 5500 than the collapsed clamping structure 5100 of FIG. 6B would have formed. Therefore, where such proper fit of curvature between the concave side and contoured object is desired, the control of curvature by installing and removing detachable segments may be useful. In some embodiments, the clamping structure may show gradually greater clamping activity as one, two, three and more detachable segments are installed, so that the user of the clamping structure may adjust the degree of clamping activity by removing or installing the detachable structure. In other embodiments, the clamping structure may be designed to clamp in smaller degree with the detachable segments installed.

Figure 8A:
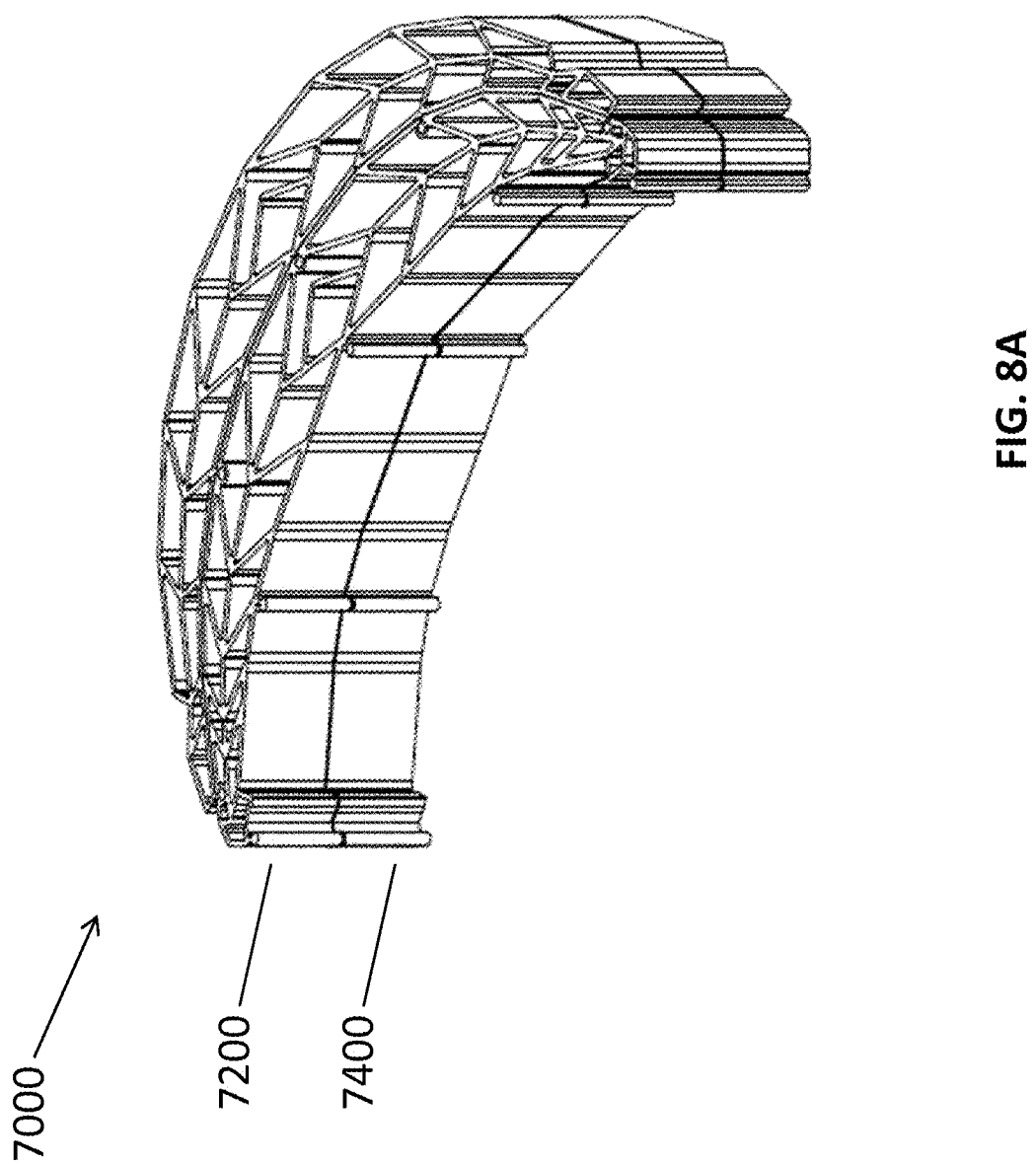
FIGS. 8A-B illustrate a perspective view and an exploded view of an embodiment of stacked clamping structures.
Figure 8B:
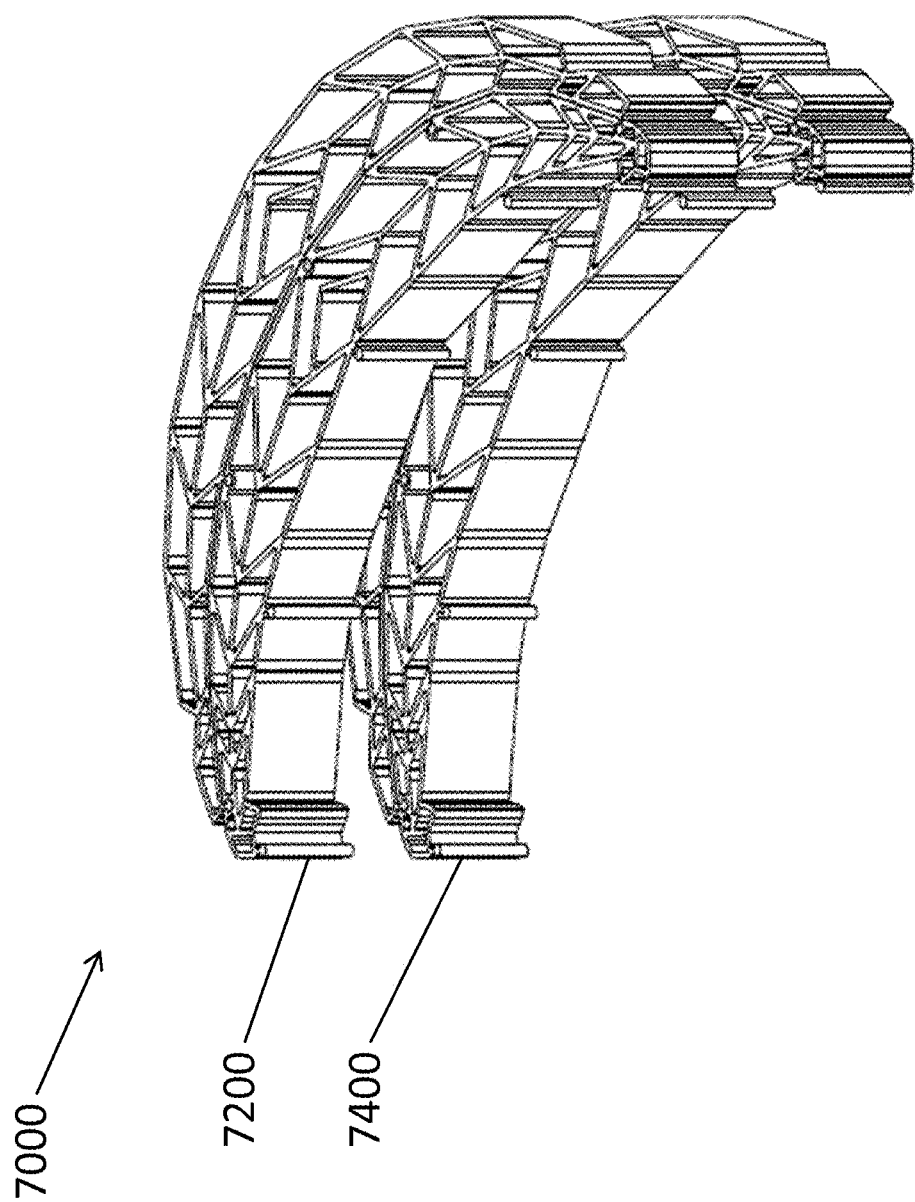
Figure 8C:
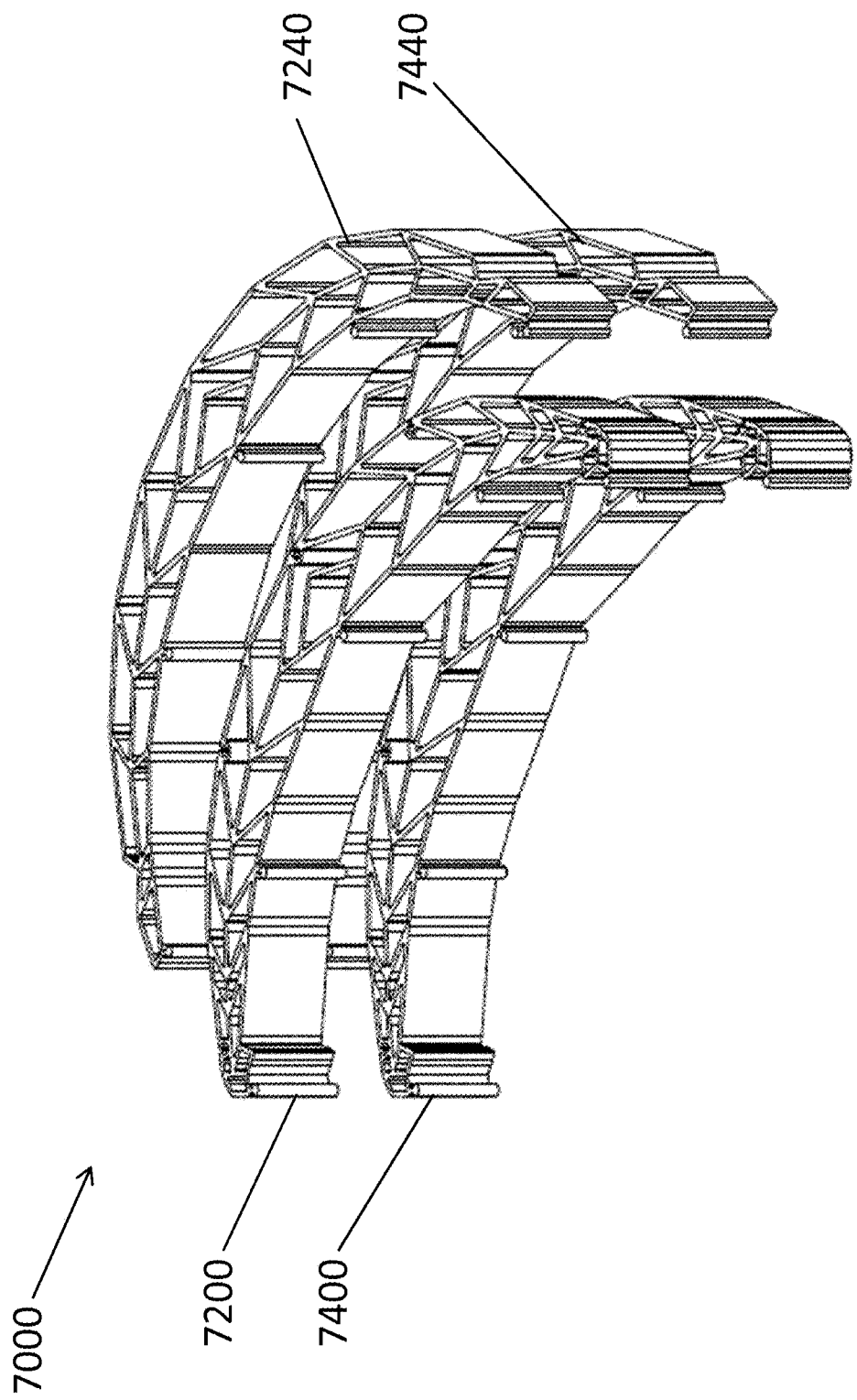
FIG. 8C illustrates an exploded view of an embodiment of stacked clamping structures.

FIG. 8A-C: Stackable Clamping Device

Figure 8D:
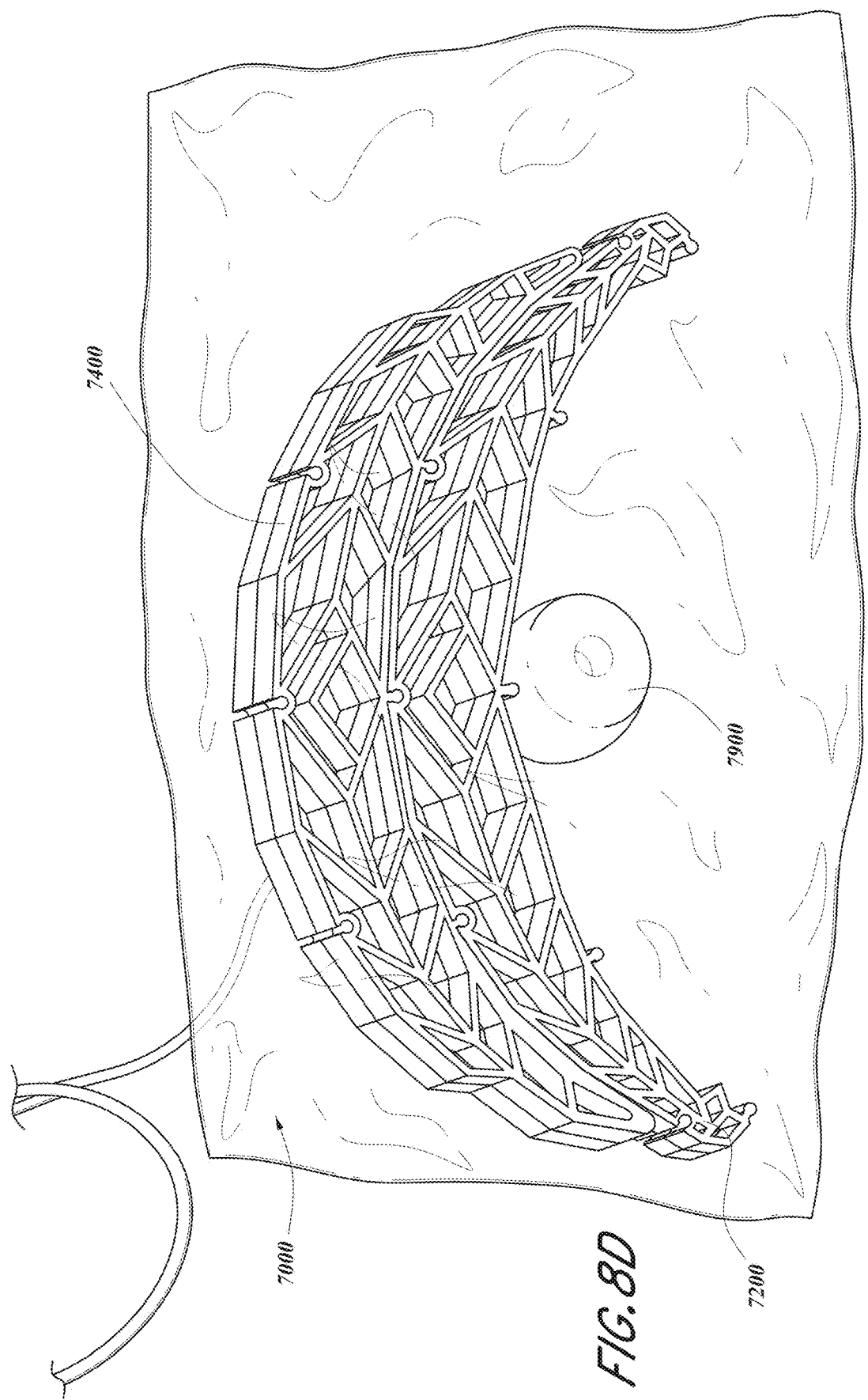
FIGS. 8D-8E are photographs of an embodiment of a stacked clamping structure.
Figure 8E:
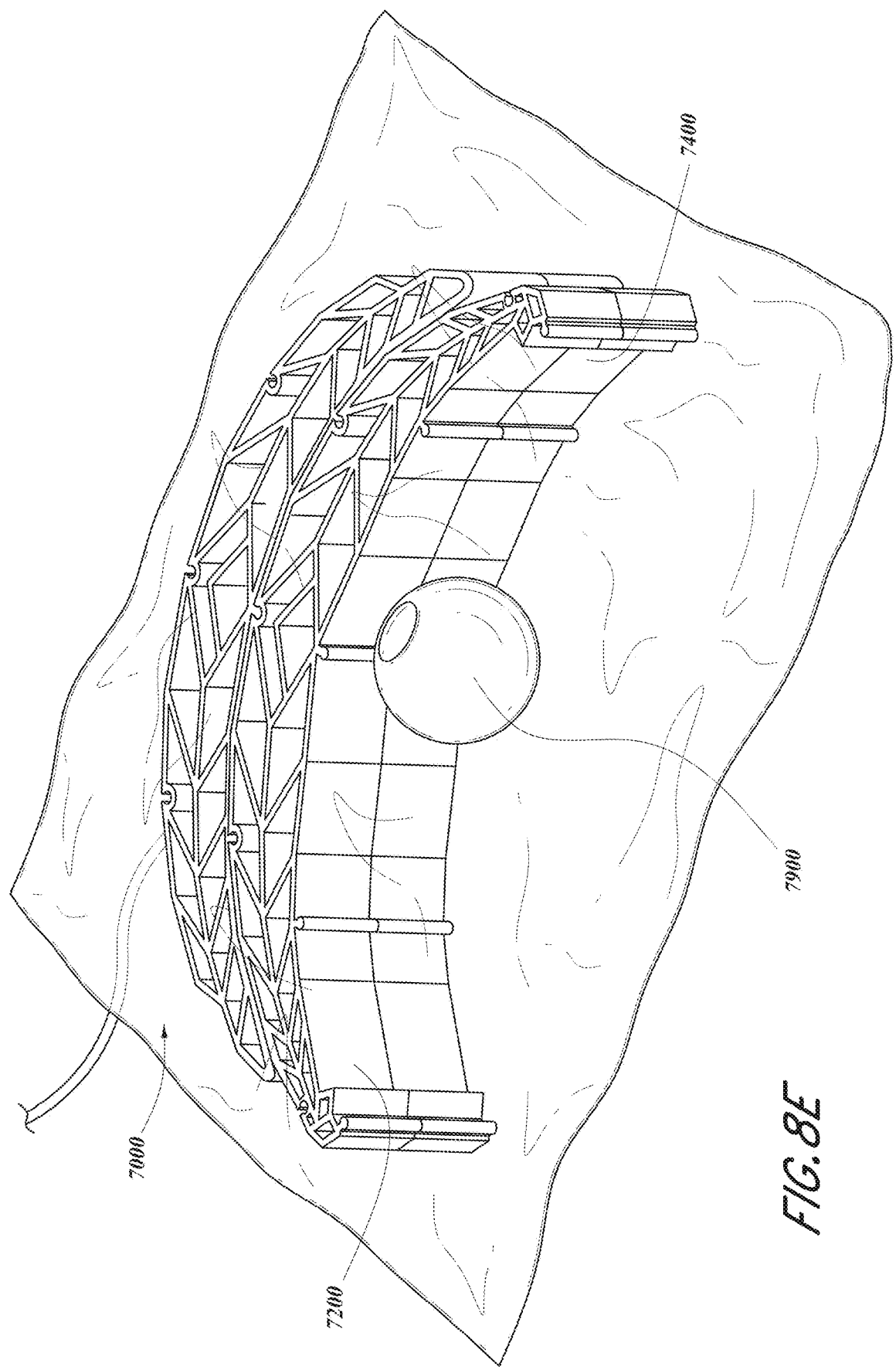

FIG. 8A depicts an embodiment of a clamping device 7000, comprising 7200 and 7400, similar to those disclosed elsewhere in the specification, such as in relation to FIGS. 2A-7D. However, here, the clamping structures 7200 and 7400 may be stacked one atop the other to provide a clamping device 7000 with greater depth. FIG. 8B illustrates an exploded view of such embodiments. In some embodiments, the clamping device may comprise two stackable clamping structures, three stackable clamping structures, four stackable clamping structures, five stackable clamping structures, or more than five stackable clamping structures. In some embodiments, all stackable clamping structures have same sizes. In other embodiments, stackable clamping structures have difference sizes. Similar to the detachable segments described above, the stackable clamping structures may be packaged separately as kits. In some embodiments, the stackable clamping structures contain attachment elements and/or receiving elements, such as those disclosed herein this section or elsewhere in the specification, thereby allowing the stackable clamping structures to be attached to one another. The attachment elements may serve to maintain attachment of one clamping structure to another clamping structure until the clamping device is re-sized by applying suitable force to separate the attachment elements from the receiving elements. The stackable clamping structures may be stacked/disassembled by application of force, for example the force of the user. In some embodiments, as shown in FIG. 8C, stackable clamping structures may further comprise detachable elements 7240 and 7440, such that user can adjust the width of the clamping device by removing/attaching the detachable elements, and adjust the height of the clamping device by removing/stacking clamping structures. FIGS. 8D and 8E are photographs of an embodiment of stackable clamping structures 7000 which is similar with the stackable clamping structures described in relation to FIGS. 8A-8C and applied around a spherical object 7900.

Figure 9B:
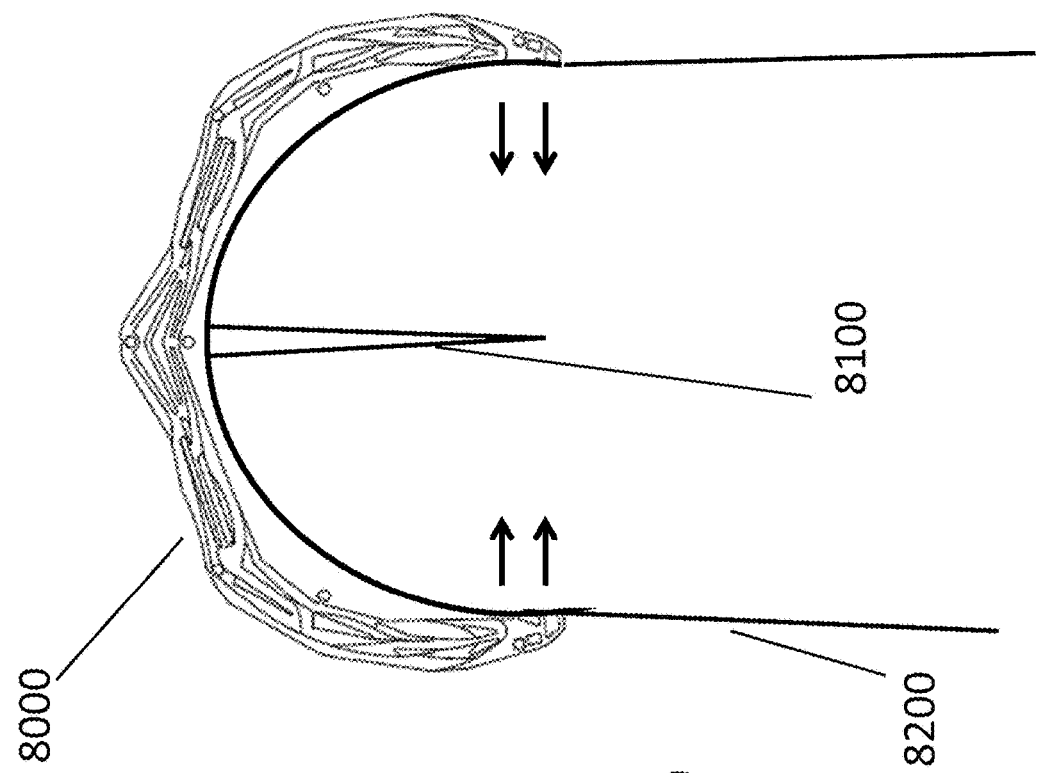
FIG. 9B illustrates the embodiment of a clamping structure of FIG. 9A in a collapsed state and the amputation wound of FIG. 9A.
Figure 9A:
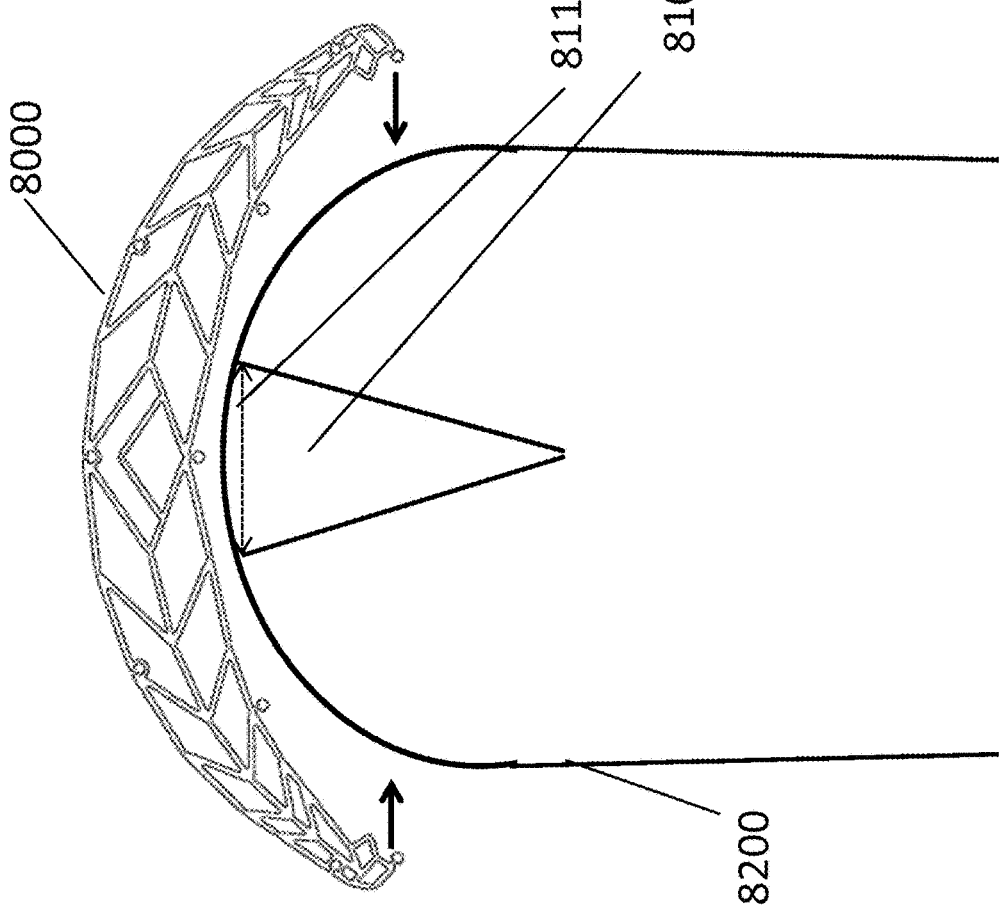
FIG. 9A illustrates an embodiment of a clamping structure in a natural state and an amputation wound.

FIGS. 9A-B: Wound Closure Device and Treatment Methods

The clamping structures and/or wound closure devices described in this section or elsewhere in this specification may be used in conjunction with methods or systems for the closure of a wound, for example an amputation wound or wounds at the extremities. In some embodiments, one or more of the clamping structures or wound closure devices of any of the embodiments described in this section or elsewhere in this specification may be placed over a wound. In some embodiments, an organ protection layer may be provided in the wound before placement of the stabilizing structure. In certain embodiments, foam or other porous material may be placed in or on the wound along with the clamping structure or wound closure device, either below, above, or surrounding the clamping structure or wound closure device. Foam or other porous material may also surround the perimeter of the clamping structure or wound closure device. The clamping structure or wound closure device may be configured to collapse in any manner as described in this section or elsewhere in this specification, for example by having a particular size and shape. The clamping structure or wound closure device may further be altered in any manner described in this section or elsewhere in this specification so as to better accommodate the shape of the wound. After placement on the wound, the clamping structure or wound closure device can be sealed by a fluid-tight drape. The fluid-tight drape can comprise a port configured for the application of negative pressure. A source of negative pressure may then be connected to the port and negative pressure may be applied to the wound. The clamping structure or wound closure device may be replaced over time by clamping or wound closure devices of various shapes and sizes as desired to best promote wound healing.

FIGS. 9A-B are schematic illustrations depicting embodiments of methods for treatment of a wound 8100 that utilize a wound closure device comprising a clamping structure 8000. The clamping structure 8000 may be a clamping structure such as those disclosed herein this section and elsewhere in the specification, such as described above in relation to FIGS. 2A-8E. The wound 8100 depicted in FIGS. 8A-B may be a large wound at the extremity 8200. In some embodiments, the wound 8100 can be an amputation wound, although such method is not limited to any certain type of wound. In some instances, as described elsewhere in the specification, such wound may be produced via a surgical amputation or other means. In certain embodiments, the amputated portion may be a finger, hand, arm, toe, foot, or leg. In certain embodiments, as described in greater detail below, a clamping structure such as those disclosed above in relation to FIGS. 2A-8C may be placed on wounds on extremities to enhance closure of the wound. Before treatment, the wound may be cleaned and the skin may be prepared for application of a wound closure device.

In some embodiments, an optional tissue protection layer (not shown) may be placed over the wound to protect the underlying tissues from the rigors of negative pressure wound therapy or other potential harms. Accordingly, certain embodiments of the wound closure devices comprise a tissue protections layer which may be cut to size to be placed over the wound site 8100. The tissue protection layer can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the wound bed 8100. In further examples, materials such as the fluoropolymer polytetrafluoroethylene (PTFE) may be applicable as these materials are generally non-adherent and used in surgical grafts. In one embodiment, the tissue protection layer is permeable. For example, the tissue protection layer can be provided with openings, such as holes, slits, or channels, to allow the removal of fluids from the wound site 8100 or the transmittal of negative pressure to the wound site 8100. In certain embodiments, the tissue protection layer may comprise a sensor configured to measure pressures in and around the wound. For example, the sensor may be used to measure the level of negative pressure applied to the wound or to measure the pressure on the underlying organs beneath the abdominal wound.

In some embodiments, a bottom layer of foam (not shown) may be optionally placed over the organ protection layer. This bottom layer of foam may extend outward beneath the surface of the wound, and optionally be attached to a clamping structure placed over the foam. This bottom layer of foam may be configured to conform to the concave side of the clamping structure, so that the clamping structure can be properly positioned above the bottom layer of foam. In some embodiments, the bottom layer of foam can extend along the length of the concave side from the first end to the second end, so that the bottom layer of foam provides a cushion between the skin and the clamping structure.

In certain embodiments, such as shown in FIG. 9A, the clamping structure 8000 may be applied on the wound 8100 in the direction that the concave side faces the wound. In some embodiments, the clamping structure is aligned so that the length of the clamping structure is across the wound opening along the width of the wound 8110. The width of the wound can be defined as the size of the wound along the direction where the wound needs to be closed. A practitioner may choose a suitable clamping structure so that the size and the curvature of the clamping structure, especially of the concave side, properly fit the shape and the size of the wound. As with the clamping structures disclosed above in relation to FIGS. 4A-8C, a clamping structure placed on the wound may be adjustable by installing/removing detachable segments or stacking clamping structures to suitably fit the size and the shape of the wound. Over time, various clamping structures of different sizes may be applied as the size and shape of the wound changes during healing. In some embodiments, an optional bottom layer of foam (not shown) may be applied on the concave side of the clamping structure, and optionally be attached to a clamping structure placed above the foam. Such bottom layer of foam placed between the clamping structure and the wound may better accommodate the clamping structure to various size and shape of wounds, and may further protect the wound and tissues around from excessive force or friction exerted by the clamping structure.

FIG. 9B illustrates an embodiment of wound closure device during the treatment of the wound 8100 under negative pressure. As the clamping device 8000 collapses as described in greater detail elsewhere in this section and/or elsewhere in the specification, the curvature of the clamping device increases and the first end and the second end of the clamping device gets closer. Therefore when the first end and the second end of the clamping device is placed across the wound 8100, the clamping device 8000 enhances closure of the wound 8100 by exerting force in the direction of arrows depicted in FIG. 8B. In some embodiments, as described above in relation to FIGS. 4A-7D, the strength of the force exerted by the clamping structure on the wound site can be adjusted by installing or removing detachable segments. In some embodiments, the strength of the clamping structure may be adjusted by using clamping structures made of materials of different stiffness. In further embodiments, the clinician may adjust the size and clamping strength of the clamping structure as the wound heals over time during the therapy. Further, the vacuum level may be adjusted to modify the amount and force of collapse.

In some embodiments, an optional top layer of foam (not shown) may be applied on the convex side of the clamping structure, and optionally be attached to a clamping structure placed below the foam. In embodiments, a layer or layers of foam may be applied around the periphery of the clamping structure. In embodiments, the top layer of foam may be configured to conform to the convex side of the clamping structure, so that it can be properly applied on the clamping structure.

In certain embodiments, a drape may be applied to the top of the top foam, or directly to the top of the clamping structure, thereby forming an air-tight seal over the clamping structure, allowing for the application of negative pressure. Negative pressure may be applied to the clamping structure for any length of time described herein this section or elsewhere in the specification, for example about: 1 hour, 6 hours, 12 hours, 24 hours, 48 hours, or more than 48 hours.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombinations. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound closure device, comprising:
   a clamping structure having a first end, a second end, and a length extending from the first end to the second end, the clamping structure comprising:
   a concave side and a convex side extending the length of the clamping structure from the first end to the second end; and
   a plurality of cells provided side-by-side in a horizontal plane;
   wherein the clamping structure is configured to increase curvature along a horizontal plane parallel to the length and width of the clamping structure upon collapse of the plurality of cells under negative pressure such that the first end and the second end move closer to one another.

2. The wound closure device of claim 1, wherein the clamping structure is configured to collapse more in the horizontal plane than in a vertical plane perpendicular to the horizontal plane.

3. The wound closure device of claim 1, wherein individual cells are diamond-shaped.

4. The wound closure device of claim 1, wherein the clamping structure comprises a partial-elliptical shape.

5. The wound closure device of claim 1, wherein the concave side and the convex side are configured to bend or curve such that they are aligned in semi-parallel fashion.

6. The wound closure device of claim 1, further comprising a layer of foam configured to conform to the concave side of the clamping structure.

7. The wound closure device of claim 6, further comprising a layer of foam configured to conform to the convex side of the clamping structure.

8. The wound closure device of claim 1, further comprising a tissue protection layer.

9. A method of closing a wound, comprising:
   providing a clamping structure having a first end, a second end, and a length extending from the first end to the second end, the clamping structure comprising:
   a concave side and a convex side extending the length of the clamping structure from the first end to the second end, and
   a plurality of cells provided side-by-side in a horizontal plane;
   sealing a drape over the clamping structure; and applying negative pressure through the drape to the wound such that the negative pressure causes the plurality of cells to collapse along a horizontal plane parallel to the length and width of the clamping structure thereby increasing curvature of the clamping structure and bringing the first end and the second end closer to one another.

10. The method of claim 9, wherein collapsing of the plurality of cells promotes closure of the wound.

11. The method of claim 9, wherein the drape comprises a port configured for the application of negative pressure.

12. The method of claim 9, wherein individual cells are diamond-shaped.

13. The method of claim 9, wherein the clamping structure is configured to collapse more in the horizontal plane than in a vertical plane perpendicular to the horizontal plane.

14. The method of claim 9, further comprising conforming a layer of foam to the concave side of the clamping structure.

15. The method of claim 9, further comprising conforming a layer of foam to the convex side of the clamping structure.

16. The method of claim 9, further comprising positioning a tissue protection layer against the wound.

17. The method of claim 16, wherein the tissue protection layer comprises a biocompatible polymer.

18. The method of claim 16, wherein the tissue protection layer comprises polytetrafluoroethylene (PTFE) materials.

19. The method of claim 16, wherein the tissue protection layer further comprises a sensor configured to measure pressure in or around the wound.

\* \* \* \* \*